US008348426B2

(12) United States Patent
Tsukada et al.

(10) Patent No.: US 8,348,426 B2
(45) Date of Patent: Jan. 8, 2013

(54) OPTICAL IMAGE MEASUREMENT DEVICE AND IMAGE PROCESSING DEVICE

(75) Inventors: Hisashi Tsukada, Tokyo (JP); Hiroyuki Aoki, Tokyo (JP); Yasufumi Fukuma, Fort Lee, NJ (US); Tsutomu Kikawa, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 1209 days.

(21) Appl. No.: 12/052,187

(22) Filed: Mar. 20, 2008

(65) Prior Publication Data
US 2008/0234972 A1 Sep. 25, 2008

(30) Foreign Application Priority Data

Mar. 23, 2007 (JP) ................................. 2007-077687

(51) Int. Cl.
*A61B 3/14* (2006.01)
(52) U.S. Cl. ......... 351/206; 351/205; 351/209; 351/221
(58) Field of Classification Search .................. 382/131; 351/206; 356/497
See application file for complete search history.

(56) References Cited

U.S. PATENT DOCUMENTS

| 5,095,906 | A  | * | 3/1992 | Ema ............................... 600/407 |
| 5,524,130 | A  | * | 6/1996 | Ohhashi ........................... 378/15 |
| 6,215,848 | B1 | * | 4/2001 | Linders et al. ............. 378/98.12 |
| 6,256,370 | B1 |   | 7/2001 | Yavuz |
| 6,748,098 | B1 | * | 6/2004 | Rosenfeld ..................... 382/131 |
| 7,315,638 | B2 |   | 1/2008 | Hara |
| 7,492,466 | B2 |   | 2/2009 | Chan et al. |
| 2002/0052547 | A1 | * | 5/2002 | Toida ............................. 600/425 |
| 2002/0141255 | A1 | * | 10/2002 | Inoue ............................. 365/200 |
| 2003/0103212 | A1 |   | 6/2003 | Westphal et al. |
| 2004/0109231 | A1 |   | 6/2004 | Haisch et al. |
| 2004/0131140 | A1 |   | 7/2004 | Bruder et al. |
| 2005/0140984 | A1 | * | 6/2005 | Hitzenberger ................ 356/497 |
| 2005/0185192 | A1 |   | 8/2005 | Kim et al. |
| 2005/0254008 | A1 |   | 11/2005 | Ferguson et al. |
| 2005/0254616 | A1 | * | 11/2005 | Nakanishi et al. ................. 378/4 |
| 2006/0077395 | A1 | * | 4/2006 | Chan et al. ..................... 356/497 |
| 2006/0100527 | A1 |   | 5/2006 | Gregori et al. |
| 2006/0227333 | A1 |   | 10/2006 | Tearney et al. |
| 2007/0070295 | A1 | * | 3/2007 | Tsukada et al. ................ 351/206 |
| 2007/0159595 | A1 | * | 7/2007 | Fukuma et al. ................ 351/206 |

FOREIGN PATENT DOCUMENTS

| CN | 1539377 A | 10/2004 |
| CN | 1760663 A | 4/2006 |
| EP | 0833181 | 4/1998 |
| EP | 1 470 783 A1 | 10/2004 |

(Continued)

OTHER PUBLICATIONS

European Search Report dated Jun. 25, 2008, issued on the corresponding European application No. 08005210.3.

(Continued)

*Primary Examiner* — Alexander H Taningco
(74) *Attorney, Agent, or Firm* — Edwards Wildman Palmer LLP

(57) ABSTRACT

An optical image measurement device is configured to form a tomographic image at each of a plurality of cross sections of a measurement object, and the optical image measurement device comprises: an image processor configured to execute an arithmetic operation based on a tomographic image at one cross section of the plurality of cross sections and another tomographic image at each of one or more cross sections other than the one cross section, thereby forming a new tomographic image at the one cross section.

9 Claims, 13 Drawing Sheets

FOREIGN PATENT DOCUMENTS

| JP | 06217971 A | * | 8/1994 |
|---|---|---|---|
| JP | 2002-263098 A | | 9/2002 |
| JP | 2003-000543 | | 1/2003 |
| JP | 2004-350849 | | 12/2004 |
| JP | 2005-241464 | | 9/2005 |
| JP | 2006112864 A | | 4/2006 |
| JP | 2006212153 A | | 8/2006 |
| WO | WO-98/36691 A1 | | 8/1998 |
| WO | WO-2006022045 A1 | | 3/2006 |
| WO | WO-2006/077107 | | 7/2006 |

OTHER PUBLICATIONS

Chinese Office Action of application No. 200810084044.1, dated May 12, 2010.

Dan P. Popescu et al., "Speckle Noise Attenuation in Optical Coherence Tomography by Compounding Images Acquired at Different Positions of the Sample," National Research Council of Canada, Institute for Biodiagnostics; Optics Communications 269, 2007, pp. 247-251.

M. Bashkansky et al., "Statistics and Reduction of Speckle in Optical Coherence Tomography," Optics Letters, vol. 25, No. 8, Apr. 15, 2000, pp. 545-547.

B Sander et al. "Enhanced Optical Coherence Tomography Imaging by Multiple Scan Averaging," J Ophthalmol 2005, 89, Jul. 7, 2004, pp. 207-212.

S. H. Xiang et al., "Speckle Noise Reduction for Optical Coherence Tomography," SPIE vol. 3196, Jan. 31, 1998, pp. 79-88.

J. M. Schmitt et al., "Speckle in Optical Coherence Tomography," Journal of Biomedical Optics, Jan. 1999, vol. 4, No. 1, pp. 95-105.

Notice of Opposition dated Mar. 29, 2011, issued for the corresponding European patent application No. 08005210.3.

* cited by examiner

OPTICAL IMAGE MEASUREMENT DEVICE AND IMAGE PROCESSING DEVICE

BACKGROUND OF THE INVENTION

1. Field of the Invention

The present invention relates to an optical image measurement device and image processing device for imaging the morphology of a measurement object of a light-scattering medium, based on the reflected light or transmitted light of a light beam applied to the measurement object, and specifically relates to a technique that is favorably applicable to a fundus oculi observation.

2. Description of the Related Art

As a device for observing the fundus oculi of an eye (fundus oculi observation device), a retinal camera has been widely used conventionally. FIG. 12 shows an example of the appearance of a general retinal camera used conventionally. FIG. 13 shows an example of the configuration of an optical system internally accommodated in the retinal camera (see Japanese Unexamined Patent Application Publication JP-A 2004-350849, for example). Herein, an "observation" includes at least an observation of a captured fundus oculi image (a fundus oculi observation with a naked eye may be included).

First, referring to FIG. 12, the appearance of a conventional retinal camera 1000 will be described. This retinal camera 1000 is provided with a platform 3 mounted on a base 2 so as to be slidable in the front and rear, right and left directions (horizontal directions). On this platform 3, an operation panel and a control lever 4 for an examiner to perform various operations are mounted.

The examiner can 3-dimensionally move the platform 3 on the base 2 by operating the control lever 4. On the top of the control lever 4, an operation button 4a pressed down at the time of capturing a fundus oculi is mounted.

On the base 2, a post 5 is mounted standing upward. This post 5 is provided with a jaw rest 6 where a jaw of a subject is rested, and an external fixation lamp 7 serving as a light source for fixing an eye E.

On the platform 3, a main body part 8 is placed for accommodating various optical systems and control systems of the retinal camera 1000. The control system may be placed, for example, inside the base 2 or the platform 3, or in an external device such as a computer connected to the retinal camera 1000.

On the eye E side of the main body part 8 (i.e., on the left side on the sheet of FIG. 12), an objective lens part 8a placed facing the eye E is disposed. Moreover, on the examiner's side (i.e., on the right side on the sheet of FIG. 12), an eyepiece part 8b for observing the fundus oculi of the eye E with naked eyes is disposed.

Furthermore, to the main body part 8, a still camera 9 for producing a still image of the fundus oculi of the eye E and an imaging device 10 such as a TV camera for producing a still image or moving image of the fundus oculi are disposed. The still camera 9 and the imaging device 10 are formed so as to be removable from the main body part 8.

As the still camera 9, in accordance with various conditions such as the purpose of an examination and a method of saving a captured image, a digital camera equipped with an imaging device such as a CCD (charge coupled device) and a CMOS (complementary metal oxide semiconductor), a film camera, an instant camera and the like may be interchangeably used as necessary. The main body part 8 is provided with a mounting part 8c for interchangeably mounting the still camera 9.

In a case where the still camera 9 and the imaging device 10 are of digital imaging type, it is possible to send image data of fundus oculi images captured by these components to a computer or the like connected to the retinal camera 1000, and observe by displaying the fundus oculi images on a display. Further, it is possible to send the image data to an image recording device connected to the retinal camera 1000 and create a database, and use it as, for example, electronic data for creating an electronic medical record.

Further, on the examiner's side of the main body part 8, a touch panel monitor 11 is disposed. On this touch panel monitor 11, a fundus oculi image of the eye E formed based on video signals outputted from the (digital-type) still camera 9 or imaging device 10 is displayed. Moreover, on the touch panel monitor 11, an x-y coordinate system taking the center of a screen as the origin is displayed superimposed on the fundus oculi image. When the examiner touches the screen, coordinate values corresponding to a touched position are displayed.

Next, referring to FIG. 13, the configuration of the optical system of the retinal camera 1000 will be described. The retinal camera 1000 is provided with an illumination optical system 100 that illuminates a fundus oculi Ef of the eye E, and an imaging optical system 120 that guides the illumination light reflected by the fundus oculi to the eyepiece part 8b, the still camera 9 and the imaging device 10.

The illumination optical system 100 comprises: an observation light source 101; a condenser lens 102; an imaging light source 103; a condenser lens 104; exciter filters 105 and 106; a ring transparent plate 107; a mirror 108; an LCD 109; an illumination diaphragm 110; a relay lens 111; an aperture mirror 112; and an objective lens 113.

The observation light source 101 is composed of, for example, a halogen lamp, and emits continuous light for fundus oculi observation. The condenser lens 102 is an optical element for converging the continuous light (observation illumination light) emitted by the observation light source 101 and almost evenly applying the observation illumination light to the fundus oculi Ef.

The imaging light source 103 is composed of, for example, a xenon lamp, and is flashed at the time of imaging of the fundus oculi Ef. The condenser lens 104 is an optical element for converging the flash light (imaging illumination light) emitted by the imaging light source 103 and evenly applying the imaging illumination light to the fundus oculi Ef.

The exciter filters 105 and 106 are filters used at the time of fluorography of an image of the fundus oculi Ef. The exciter filters 105 and 106 can be respectively inserted into and removed from an optical path by a drive mechanism (not illustrated) such as a solenoid. The exciter filter 105 is placed on the optical path at the time of FAG (fluorescein angiography). The exciter filter 106 is placed on the optical path at the time of ICG (indocyanine green angiography). At the time of color-imaging, both the exciter filters 105 and 106 are retracted from the optical path.

The ring transparent plate 107 is placed in a conjugating position with a pupil of the eye E, and is provided with a ring transparent part 107a taking the optical axis of the illumination optical system 100 as the center. The mirror 108 reflects the illumination light emitted by the observation light source 101 or imaging light source 103, in a direction of the optical axis of the imaging optical system 120. The LCD 109 displays a fixation target (not illustrated) for fixing the eye E.

The illumination diaphragm 110 is a diaphragm member to shut out part of the illumination light in order to prevent flare and the like. This illumination diaphragm 110 is configured so as to be movable in the optical axis direction of the illumination optical system 100, and is thus capable of changing an illumination region of the fundus oculi Ef.

The aperture mirror 112 is an optical element that combines the optical axis of the illumination optical system 100 and the optical axis of the imaging optical system 120. In the center region of the aperture mirror 112, an aperture 112a is opened. The optical axis of the illumination optical system 100 and the optical axis of the imaging optical system 120 cross each other at a substantially central position of the aperture 112a. The objective lens 113 is installed in the objective lens part 8a of the main body part 8.

The illumination optical system 100 having such a configuration illuminates the fundus oculi Ef in the following manner. First, at the time of fundus oculi observation, the observation light source 101 is turned on and an observation illumination light is emitted. This observation illumination light is applied to the ring transparent plate 107 through the condenser lenses 102 and 104 (the exciter filters 105 and 106 are retracted from the optical path). The light passed through the ring transparent part 107a of the ring transparent plate 107 is reflected by the mirror 108 and, after passing through the LCD 109, the illumination diaphragm 110 and the relay lens 111, is reflected by the aperture mirror 112. The observation illumination light reflected by the aperture mirror 112 travels in the optical axis direction of the imaging optical system 120, and is converged by the objective lens 113, thereby entering the eye E and illuminate the fundus oculi Ef.

At this moment, since the ring transparent plate 107 is placed in a conjugating position with the pupil of the eye E, a ring-shaped image of the observation illumination light entering the eye E is formed on the pupil. The entering fundus oculi reflection light of the entered observation illumination light is emitted from the eye E through a central dark part of the ring-shaped image on the pupil. Thus, the observation illumination light entering the eye E is prevented from affecting the fundus oculi reflection light of the observation illumination light.

On the other hand, at the time of imaging of the fundus oculi Ef, flush light is emitted from the imaging light source 103, and the imaging illumination light is applied to the fundus oculi Ef through the same path. In the case of fluorography, either the exciter filter 105 or the exciter filter 106 is selectively placed on the optical path, depending on whether FAG imaging or ICG imaging is carried out.

Next, the imaging optical system 120 will be described. The imaging optical system 120 comprises: an objective lens 113; an aperture mirror 112 (an aperture 112a thereof); an imaging diaphragm 121; barrier filters 122 and 123; a variable magnifying lens 124; a relay lens 125; an imaging lens 126; a quick return mirror 127; and an imaging media 9a. Herein, the imaging media 9a is an imaging media (a CCD, camera film, instant film or the like) for the still camera 9.

The fundus oculi reflection light of the illumination light exiting from the eye E through the central dark part of the ring-shaped image formed on the pupil enters the imaging diaphragm 121 through the aperture 112a of the aperture mirror 112. The aperture mirror 112 reflects cornea reflection light of the illumination light, and acts so as not to mix the cornea reflection light into the fundus oculi reflection light entering the imaging diaphragm 121. Consequently, generation of flare in observation images and captured images is inhibited.

The imaging diaphragm 121 is a plate-shaped member having a plurality of circular light-transmitting parts of different sizes. The plurality of light-transmitting parts compose diaphragms with different diaphragm values (F values), and are placed alternatively on the optical path by a drive mechanism (not illustrated).

The barrier filters 122 and 123 can be inserted into and removed from the optical path by a drive mechanism (not illustrated) such as a solenoid. In FAG imaging, the barrier filter 122 is placed on the optical path, whereas in ICG imaging, the barrier filter 123 is placed on the optical path. Further, at the time of color-imaging, both the barrier filters 122 and 123 are retracted from the optical path.

The variable magnifying lens 124 is movable in the optical axis direction of the imaging optical system 120 by a drive mechanism (not illustrated). This makes it possible to change an observation magnifying ratio and an imaging magnifying ratio, and to focus images of the fundus oculi. The imaging lens 126 is a lens that focuses the fundus oculi reflection light from the eye E onto the imaging media 9a.

The quick return mirror 127 is disposed so as to be capable of being rotated around a rotary shaft 127a by a drive mechanism (not illustrated). In a case where imaging of the fundus oculi Ef is performed with the still camera 9, the fundus oculi reflection light is guided to the imaging media 9a by springing up the quick return mirror 127 that is obliquely mounted on the optical path. Meanwhile, in a case where imaging of the fundus oculi is performed with the imaging device 10, or in a case where observation of the fundus oculi is performed with the naked eye of the examiner, the quick return mirror 127 is obliquely mounted on the optical path to upwardly reflect the fundus oculi reflection light.

The imaging optical system 120 is further provided with, for guiding the fundus oculi reflection light reflected by the quick return mirror 127, a field lens 128, a switching mirror 129, an eyepiece 130, a relay lens 131, a reflection mirror 132, an imaging lens 133, and an image pick-up element 10a. The image pick-up element 10a is an image pick-up element such as a CCD installed in the imaging device 10. On the touch panel monitor 11, a fundus oculi image Ef' imaged by the image pick-up element 10a is displayed.

The switching mirror 129 is rotatable around a rotary shaft 129a in the same manner as the quick return mirror 127. This switching mirror 129 is obliquely disposed on the optical path during observation with the naked eye, thereby reflecting and guiding the fundus oculi reflection light to the eyepiece 130.

Further, at the time of capture of a fundus oculi image by using the imaging device 10, the switching mirror 129 is retracted from the optical path, and the fundus oculi reflection light is guided toward the image pick-up element 10a. In this case, the fundus oculi reflection light is passed through the relay lens 131 and reflected by the mirror 132, whereby an image is formed in the image pick-up element 10a by the imaging lens 133.

This retinal camera 1000 is a fundus oculi observation device used for observing the state of the surface of the fundus oculi Ef, namely, the state of the retina. In other words, the retinal camera 1000 is a device for acquiring a 2-dimensional fundus oculi image when the fundus oculi Ef is seen from the cornea of the eye E. On the other hand, organs such as the choroidea and the sclera exist in the deeper layers of the retina. There has been a demand for a technique for observing the state of these organs, and in recent years, there has been progress in the practical utilization of devices for observing these deeper layer organs (refer to Japanese Unexamined Patent Application Publications Nos. JP-A 2003-000543 and JP-A 2005-241464).

Each of the devices disclosed in JP-A 2003-000543 and JP-A 2005-241464 is an optical image measurement device to which a so-called OCT (Optical Coherence Tomography)

technology is applied (referred to as an optical coherence topography device, or the like). Such an optical image measurement device is a device that splits low-coherence light into two, guides one (signal light) of the lights to the fundus oculi and the other (reference light) to a given reference object, and detects and analyzes interference light obtained by superimposing the signal light passed through the fundus oculi and the reference light reflected by the reference object, thereby forming tomographic images of the surface and deep layer tissue of the fundus oculi or 3-dimensional images of the fundus oculi.

However, such a conventional optical image measurement device is configured so as to form a tomographic image based on light (signal light) having passed through a single cross-sectional position of a measurement object, so that a tomographic image with insufficient image quality may be formed. Specifically, in a case where the image quality of an image subjected to diagnosis of living organs such as a fundus oculi is insufficient, there is the possible risk of situations in which the form of the living organs cannot be captured in detail or small lesions are overlooked.

The present invention is for solving such problems, and an object of the present invention is to provide an optical image measurement device and an image processing device that are capable of enhancing the image quality of an image to be formed.

In order to achieve the aforementioned object, in a first aspect of the present invention, an optical image measurement device is configured to form a tomographic image at each of a plurality of cross sections of a measurement object, and the optical image measurement device comprises: an image processor configured to execute an arithmetic operation based on a tomographic image at one cross section of the plurality of cross sections and another tomographic image at each of one or more cross sections other than the one cross section, thereby forming a new tomographic image at the one cross section.

In a second aspect of the present invention, an image processing device comprises: a storage configured to store a tomographic image at each of a plurality of cross sections of a measurement object; and an image processor configured to execute an arithmetic operation based on a tomographic image at one cross section of the plurality of cross sections and another tomographic image at each of one or more cross sections other than the one cross section, thereby forming a new tomographic image at the one cross section.

According to the present invention, the device is configured to execute an arithmetic operation based on a tomographic image along one cross-section among a plurality of cross-sections and other tomographic images along one or more cross-sections other than the one cross-section, thereby forming a new tomographic image along the one cross-section. Therefore, it is possible to enhance the image quality of an image to be formed, as compared with in a conventional configuration in which an image is formed only from the result of measurement along a single cross-section.

DESCRIPTION OF THE DRAWINGS

FIG. 6A shows an example of the scanning mode of the signal light when a fundus oculi is seen from the incident side of the signal light with respect to an eye. FIG. 6B shows an example of a mode of arrangement of scanning points on each scanning line.

DETAILED DESCRIPTION OF THE PREFERRED EMBODIMENT

Figure 1:
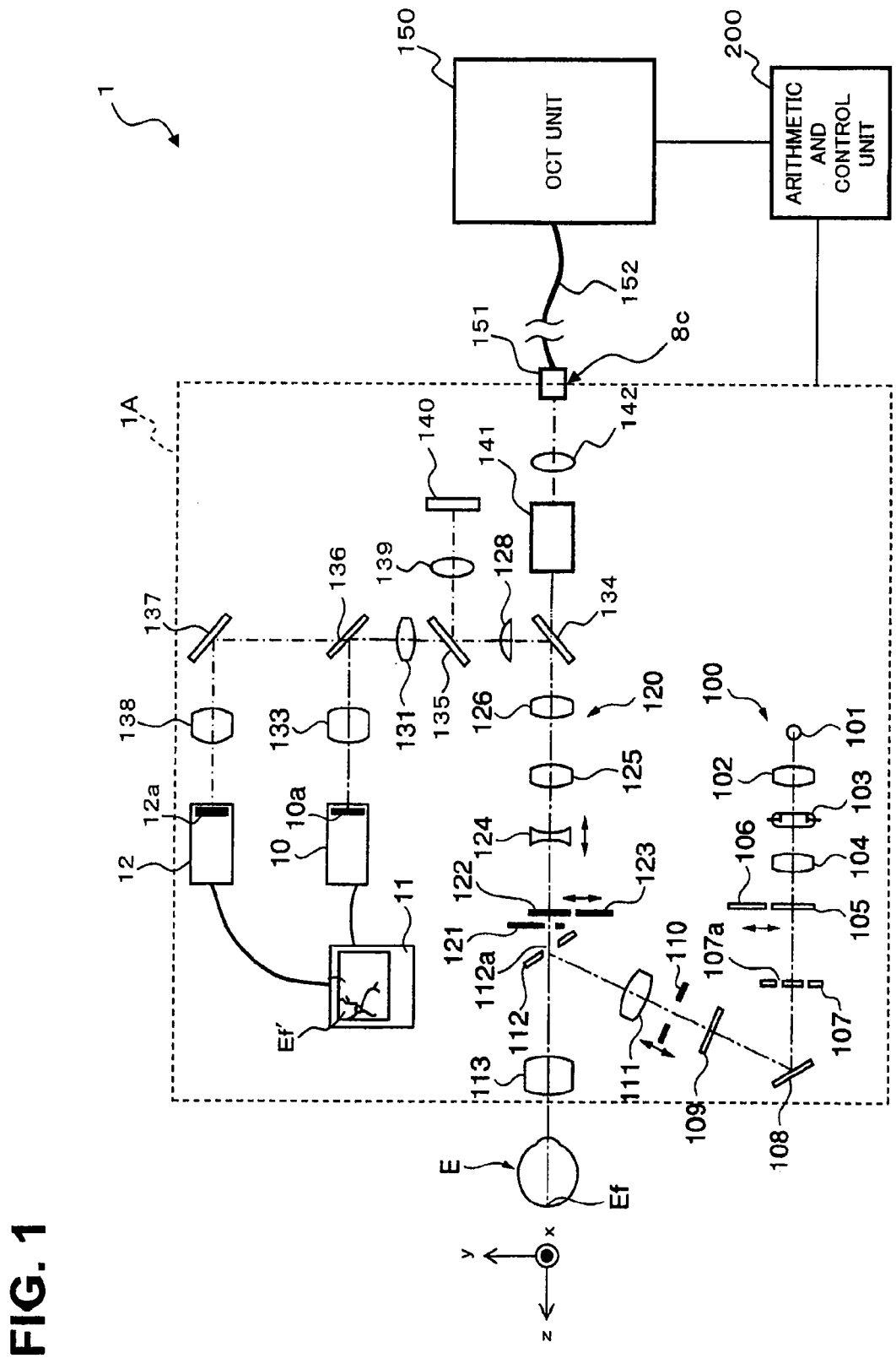
FIG. 1 is a schematic diagram showing an example of the entire configuration in a preferred embodiment of a fundus oculi observation device comprising an optical image measurement device according to the present invention.

An example of a preferred embodiment of an optical image measurement device and an image processing device according to the present invention will be described in detail referring to the drawings. Herein, the same components as the conventional ones will be denoted by the same reference symbols used in FIGS. 12 and 13.

Figure 2:
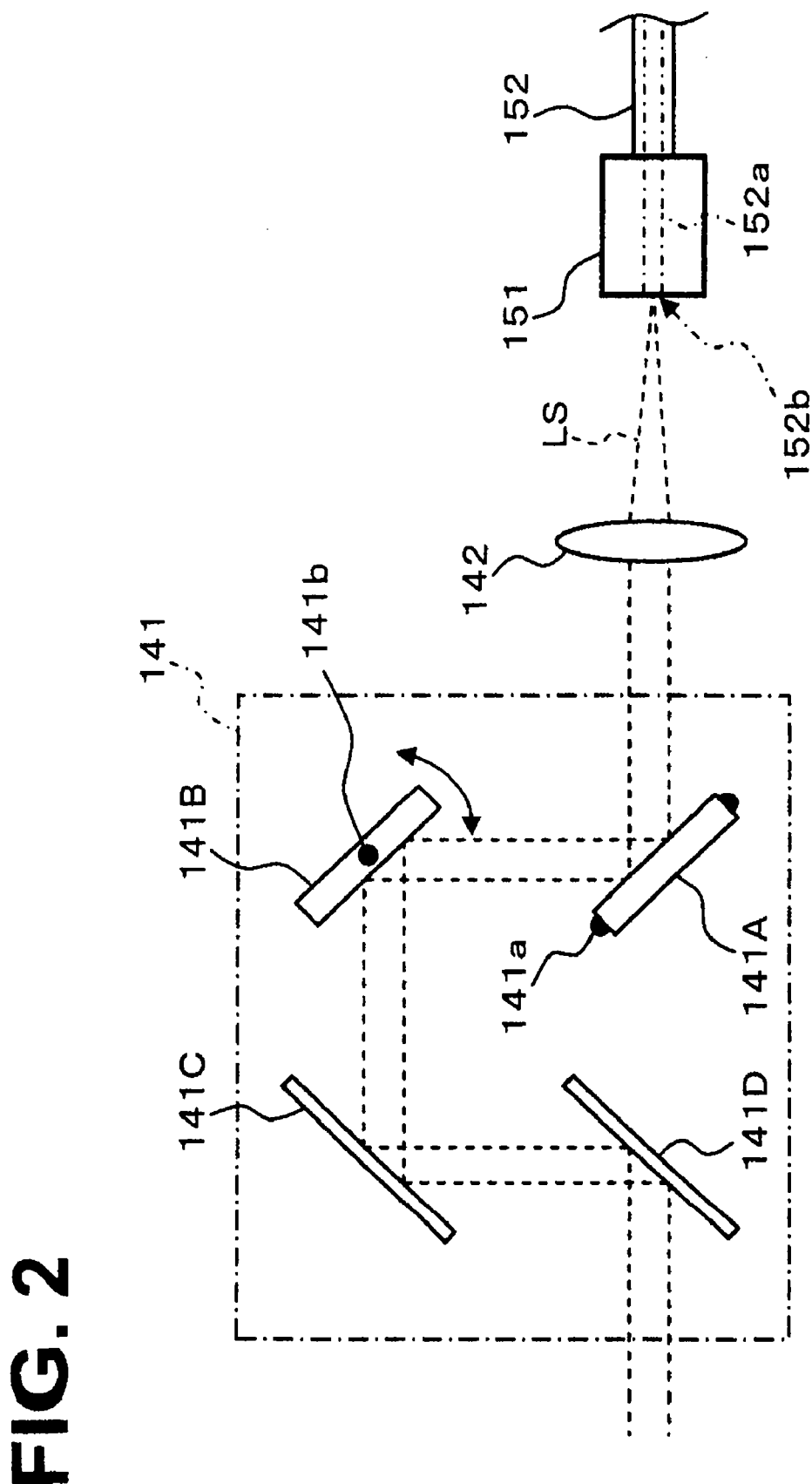
FIG. 2 is a schematic diagram showing an example of the configuration of a scanning unit installed in a retinal camera unit in the preferred embodiment of the fundus oculi observation device comprising the optical image measurement device according to the present invention.
Figure 3:
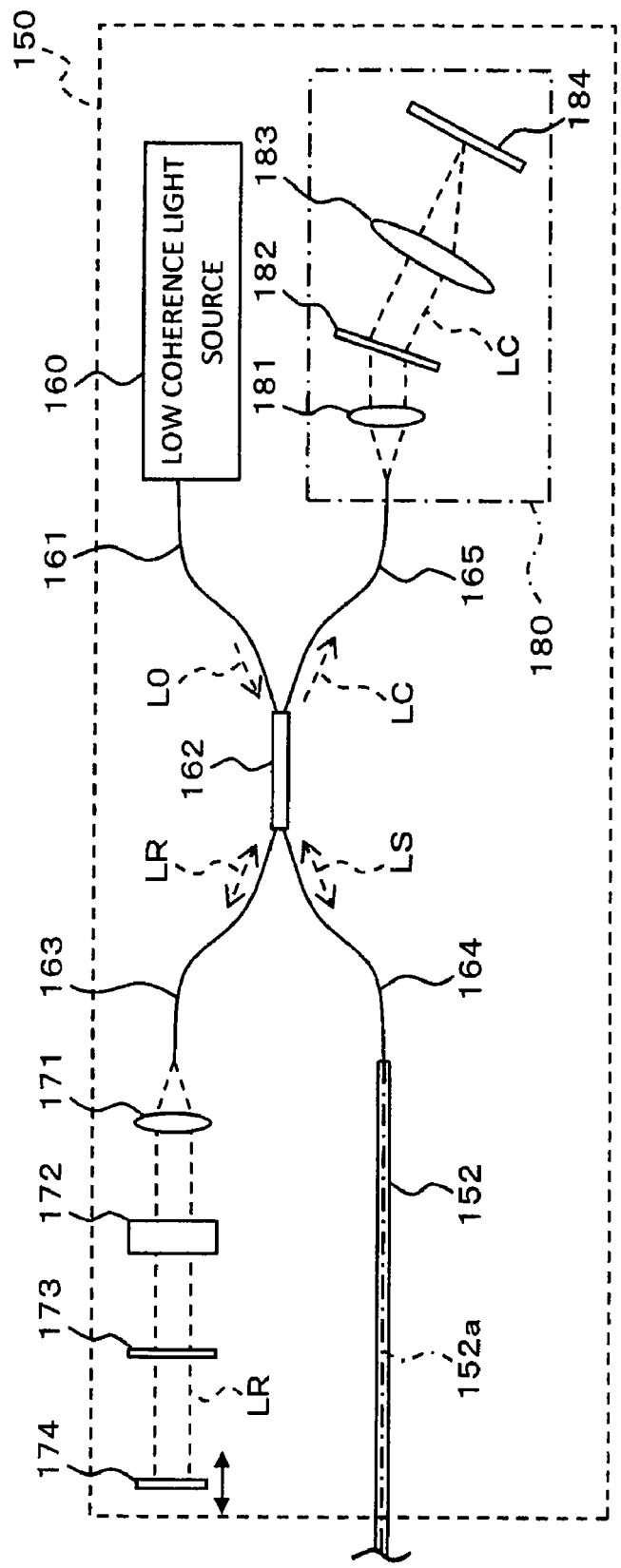
FIG. 3 is a schematic diagram showing an example of the configuration of an OCT unit in the preferred embodiment of the fundus oculi observation device comprising the optical image measurement device according to the present invention.
Figure 4:
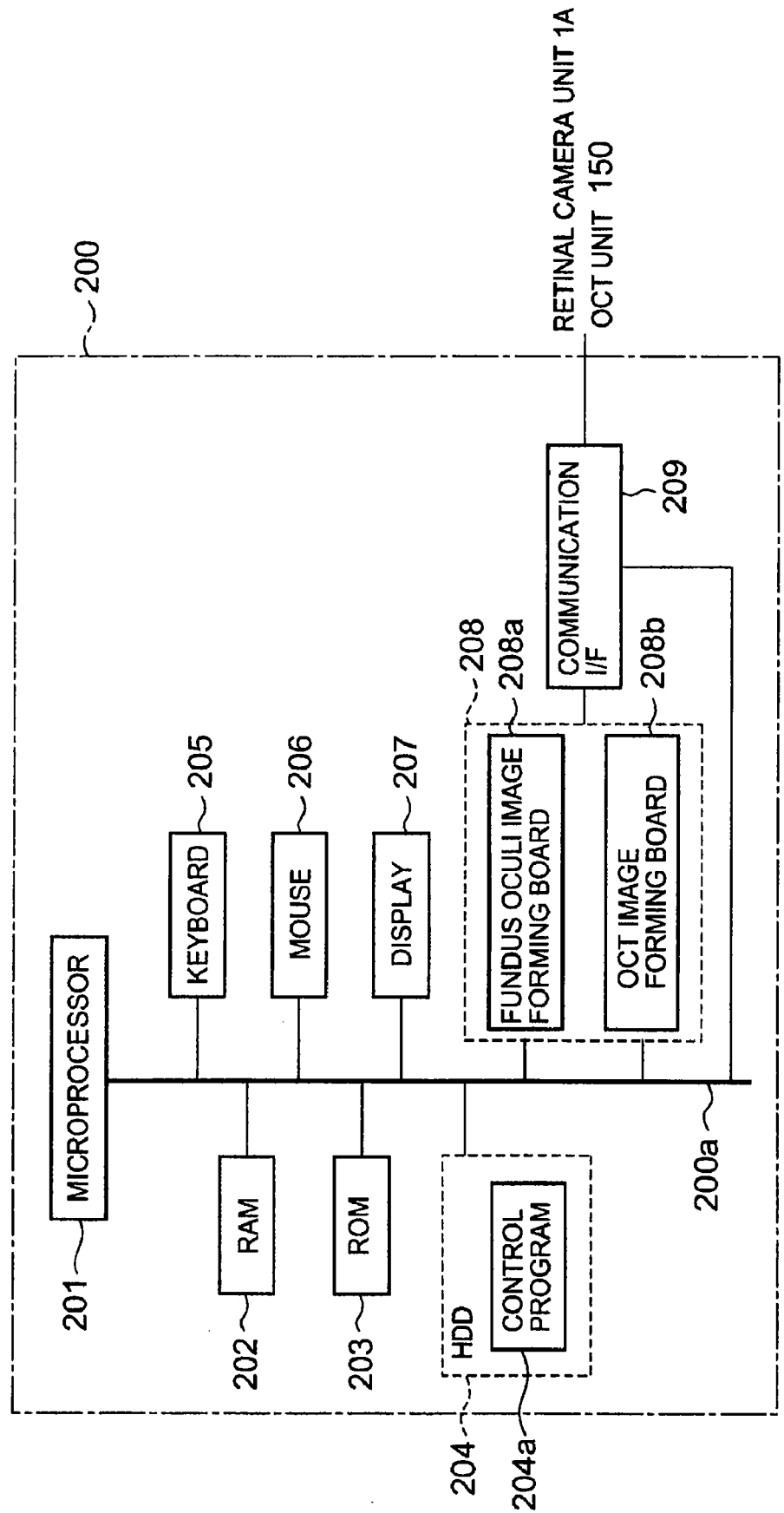
FIG. 4 is a schematic block diagram showing an example of the hardware configuration of an arithmetic and control unit in the preferred embodiment of the fundus oculi observation device comprising the optical image measurement device according to the present invention.
Figure 5:
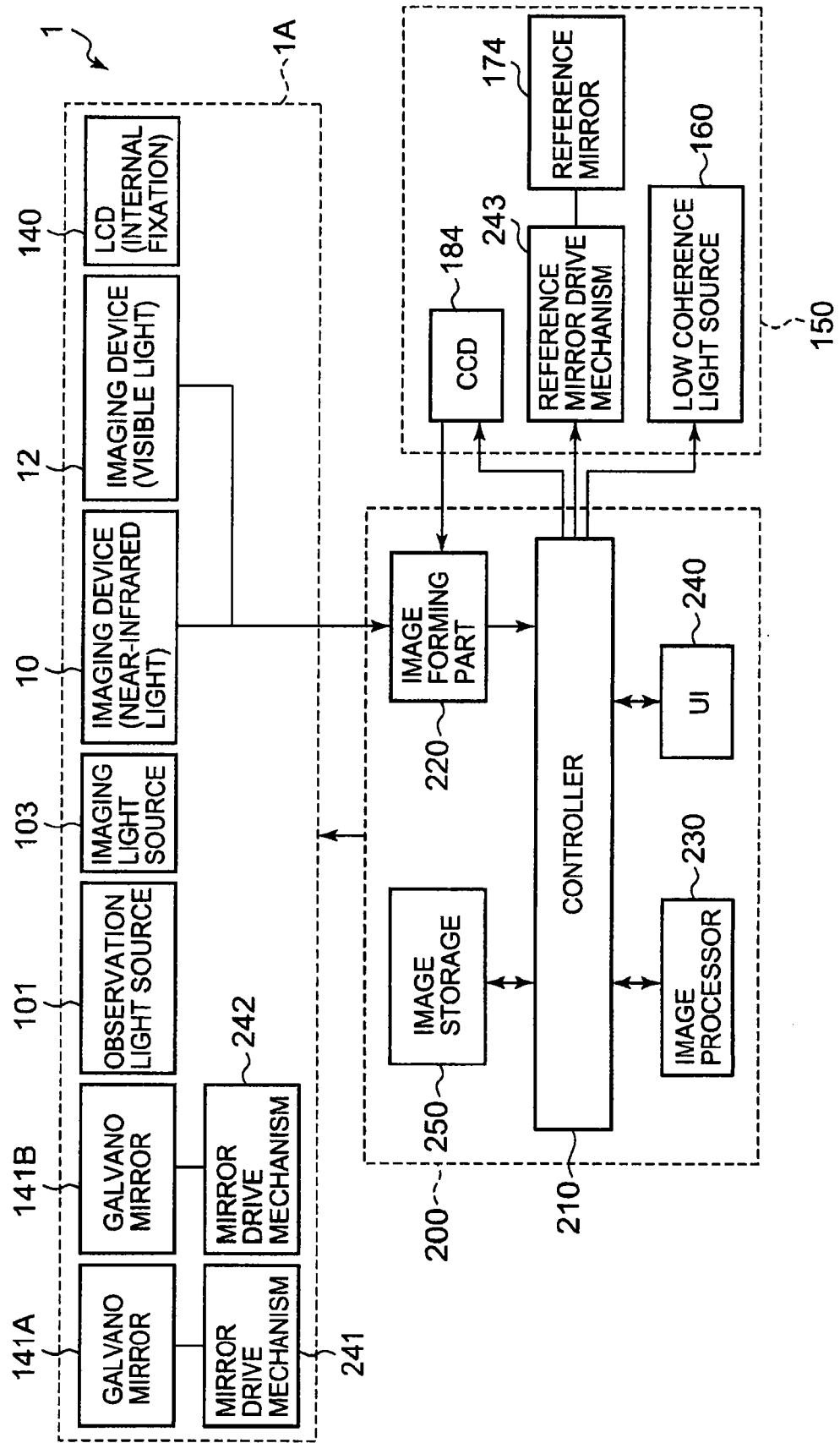
FIG. 5 is a schematic block diagram showing an example of the configuration of a control system in the preferred embodiment of the fundus oculi observation device comprising the optical image measurement device according to the present invention.

First, referring to FIGS. 1 through 5, an example of the configuration in an embodiment of the optical image measurement device according to the present invention will be described. FIG. 1 shows the entire configuration of a fundus oculi observation device 1 having a function of an optical image measurement device and a function of a retinal camera. FIG. 2 shows the configuration of a scanning unit 141 in a retinal camera unit 1A. FIG. 3 shows the configuration of an OCT unit 150. FIG. 4 shows the hardware configuration of an arithmetic and control unit 200. FIG. 5 shows the configuration of a control system of the fundus oculi observation device 1.

[Configuration of Device]

As shown in FIG. 1, the fundus oculi observation device 1 comprises: the retinal camera unit 1A that has the same function as the retinal camera; the OCT unit 150 accommodating an optical system of an optical image measurement device (OCT device); and the arithmetic and control unit 200 that executes various arithmetic processes, control processes, and the like.

The OCT unit 150 composes an example of the "optical image measurement device" of the present invention, along with the arithmetic and control device 200. Further, various types of optical members (to be described later) through which signal lights pass through, such as the scanning unit 141 provided in the fundus oculi camera unit 1A, are also included in the optical image measurement device.

To the OCT unit 150, one end of a connection line 152 is attached. To the other end of the connection line 152, a connector part 151 is attached. This connector part 151 is mounted on a mounting part 8c shown in FIG. 12. Moreover, a conductive optical fiber runs through the inside of the connection line 152. Thus, the OCT unit 150 and the retinal camera unit 1A are optically connected via the connection line 152. The detailed configuration of the OCT unit 150 will be described later referring to FIG. 3.

[Configuration of Retinal Camera Unit]

Figure 12:
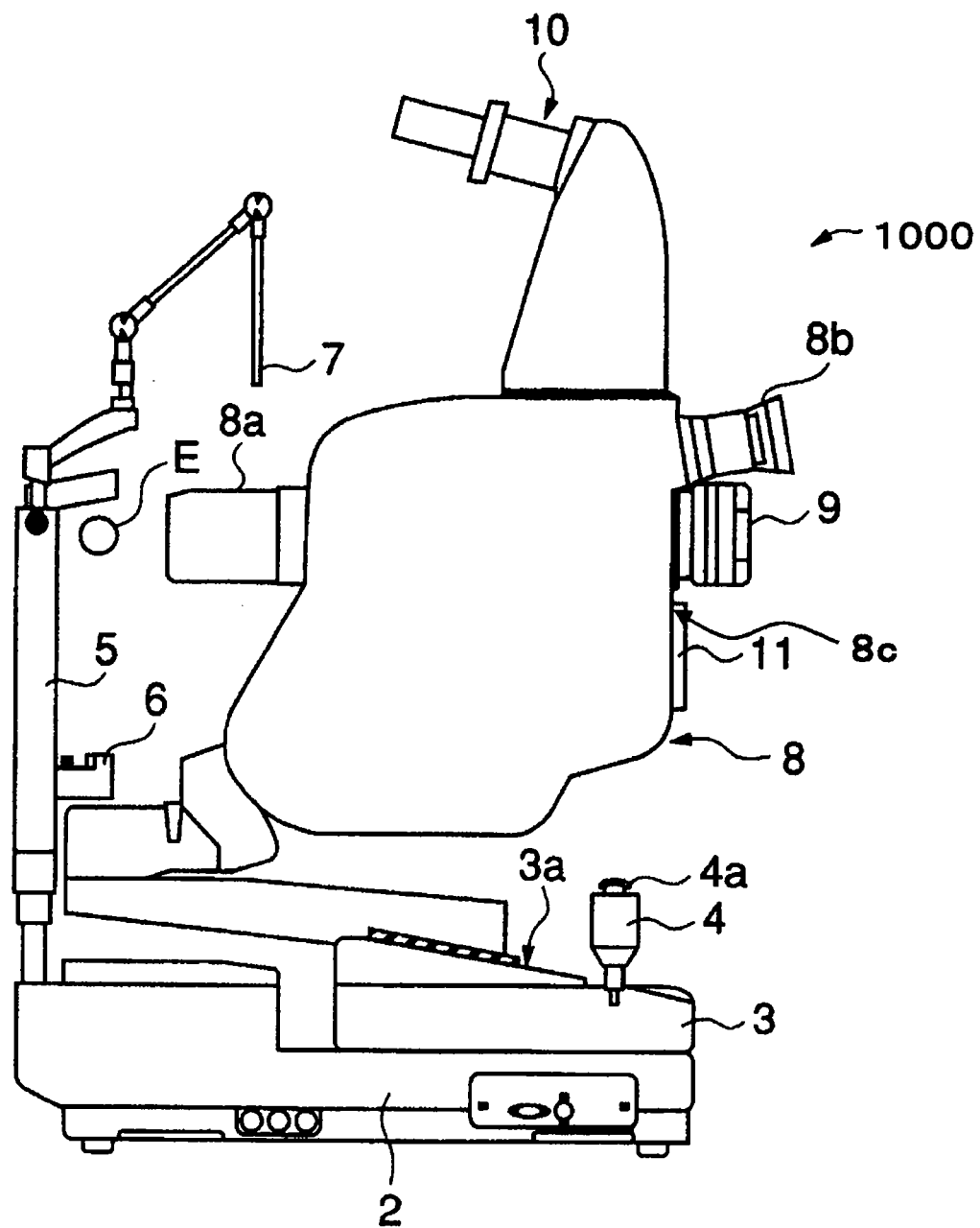
FIG. 12 is a schematic side view showing an example of the appearance of a conventional fundus oculi observation device (retinal camera).

The retinal camera unit 1A has almost the same appearance as the conventional retinal camera 1000 shown in FIG. 12. Moreover, as in the conventional optical system shown in FIG. 13, the retinal camera unit 1A is provided with an illumination optical system 100 that illuminates the fundus oculi Ef of the eye E, and an imaging optical system 120 that guides the fundus oculi reflection light of the illumination light to the imaging device 10.

Although the details will be described later, the imaging device 10 in the imaging optical system 120 of the present embodiment detects the illumination light having a wavelength in the near-infrared region. Moreover, this imaging optical system 120 is further provided with the imaging device 12 for detecting the illumination light having a wavelength in the visible region. Moreover, this imaging optical system 120 guides a signal light coming from the OCT unit 150 to the fundus oculi Ef, and guides the signal light passed through the fundus oculi Ef to the OCT unit 150.

Here, as in the conventional one, the illumination optical system 100 comprises: an observation light source 101; a condenser lens 102; an imaging light source 103; a condenser lens 104; exciter filters 105 and 106; a ring transparent plate 107; a mirror 108; an LCD 109; an illumination diaphragm 110; a relay lens 111; an aperture mirror 112; and an objective lens 113.

The observation light source 101 emits an illumination light having a wavelength of the visible region included in a range of, for example, about 400 nm thorough 700 nm. Moreover, the imaging light source 103 emits an illumination light having a wavelength of the near-infrared region included in a range of, for example, about 700 nm through 800 nm. The near-infrared light emitted from this imaging light source 103 is set so as to have a shorter wavelength than the light used by the OCT unit 150 (described later).

Further, the imaging optical system 120 comprises: an objective lens 113; an aperture mirror 112 (an aperture 112a thereof); an imaging diaphragm 121; barrier filters 122 and 123; a variable magnifying lens 124; a relay lens 125; an imaging lens 126; a dichroic mirror 134; a field lens 128; a half mirror 135; a relay lens 131; a dichroic mirror 136; an imaging lens 133; the imaging device 10 (image pick-up element 10a); a reflection mirror 137; an imaging lens 138; the imaging device 12 (image pick-up element 12a); a lens 139; and an LCD 140.

Figure 13:
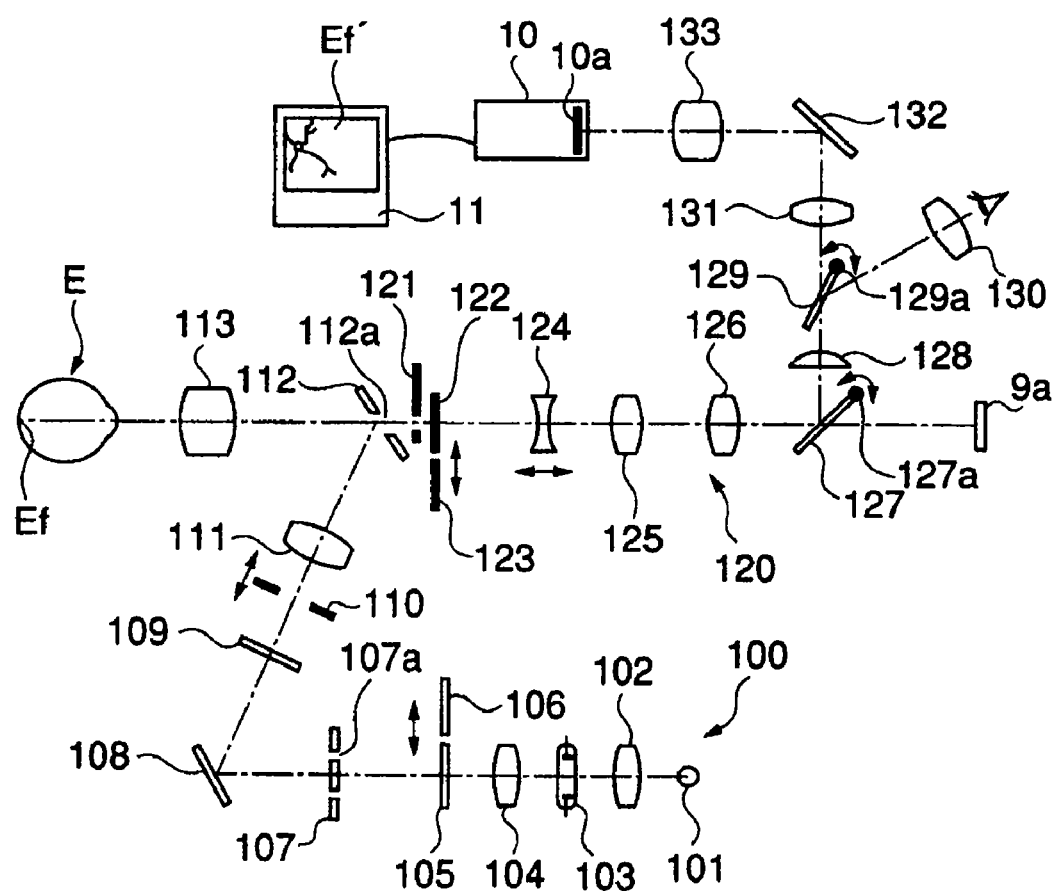
FIG. 13 is a schematic diagram showing an example of the internal configuration (optical system configuration) of a conventional fundus oculi observation device (retinal camera).

The imaging optical system 120 according to the present embodiment is different from the conventional imaging optical system 120 shown in FIG. 13 in that the dichroic mirror 134, the half mirror 135, the dichroic mirror 136, the reflection mirror 137, the imaging lens 138, the lens 139 and the LCD 140 are disposed.

The dichroic mirror 134 is configured to reflect the fundus oculi reflection light (having a wavelength included in a range of about 400 nm through 800 nm) of the illumination light from the illumination optical system 100, and transmit a signal light LS (having a wavelength included in a range of, for example, about 800 nm through 900 nm; described later) from the OCT unit 150.

Further, the dichroic mirror 136 is configured to transmit the illumination light having a wavelength of the visible region from the illumination optical system 100 (a visible light having a wavelength of about 400 nm through 700 nm emitted from the observation light source 101), and reflect the illumination light having a wavelength of the near-infrared region (a near-infrared light having a wavelength of about 700 nm through 800 nm emitted from the imaging light source 103).

On the LCD 140, an internal fixation target or the like is displayed. The light from this LCD 140 is reflected by the half mirror 135 after being converged by the lens 139, and is reflected by the dichroic mirror 136 through the field lens 128. Then, the light passes through the imaging lens 126, the relay lens 125, the variable magnifying lens 124, the aperture mirror 112 (aperture 112a thereof), the objective lens 113 and the like, and enters the eye E. Consequently, an internal fixation target or the like is projected in the fundus oculi Ef of the eye E.

The image pick-up element 10a is an image pick-up element such as a CCD and a CMOS installed in the imaging device 10 such as a TV camera, and is particularly used for detecting light having a wavelength of the near-infrared region (that is, the imaging device 10 is an infrared TV camera for detecting near-infrared light). The imaging device 10 outputs video signals as a result of detection of the near-infrared light. A touch panel monitor 11 displays a 2-dimensional image (a fundus oculi image Ef') of the surface of the fundus oculi Ef, based on the video signals. The video signals are sent to the arithmetic and control unit 200, and the fundus oculi image is displayed on the display (described later). At the time of imaging of the fundus oculi by the imaging device 10, for example, the illumination light emitted from the imaging light source 103 of the illumination optical system 100 and having a wavelength of the near-infrared region is used.

On the other hand, the image pick-up element 12a is an image pick-up element such as a CCD and a CMOS installed in the imaging device 12 such as a TV camera, and is particularly used for detecting light having a wavelength of the visible region (that is, the imaging device 12 is a TV camera for detecting visible light). The imaging device 12 outputs video signals as a result of detection of the visible light. The touch panel monitor 11 displays a 2-dimensional image (fundus oculi image Ef) of the surface of the fundus oculi Ef, based on the video signals. The video signals are sent to the arithmetic and control unit 200, and the fundus oculi image Ef is displayed on the display (described later). At the time of imaging of the fundus oculi by the imaging device 12, for example, the illumination light emitted from the observation light source 101 of the illumination optical system 100 and having a wavelength of the visible region is used.

The imaging optical system 120 according to the present embodiment is provided with 150 a scanning unit 141 and a lens 142. The scanning unit 141 includes a component for scanning at an application position of the fundus oculi Ef with light emitted from the OCT unit (signal light LS; described later).

The lens 142 makes the signal light LS guided from the OCT unit 150 through the connection line 152 enter the scanning unit 141 in the form of a parallel light flux. Moreover, the lens 142 acts so as to converge the fundus oculi reflection light of the signal light LS passed through the scanning unit 141.

FIG. 2 shows one example of a specific configuration of the scanning unit 141. The scanning unit 141 comprises Galvano mirrors 141A and 141B, and reflection mirrors 141C and 141D.

The Galvano mirrors 141A and 141B are rotatable about rotary shafts 141a and 141b, respectively. The rotary shafts 141a and 141b are disposed so as to orthogonal to each other.

In FIG. 2, the rotary shaft 141a of the Galvano mirror 141A is disposed in a direction parallel to the sheet of FIG. 2, and the rotary shat 141b of the Galvano mirror 141B is disposed in a direction parallel to the sheet of FIG. 2, and the rotary shaft 141b disposed to a direction orthogonal to the sheet of FIG. 2. That is to say, the Galvano mirror 141B is formed so as to be rotatable in the directions indicated by an arrow pointing in both directions in FIG. 2, whereas the Galvano mirror 141A is formed so as to be rotatable in the directions orthogonal to the arrow pointing in both the directions. Consequently, the pair of Galvano mirrors 141A and 141B act so as to change the reflecting directions of the signal light LS to directions orthogonal to each other.

Here, a rotation movement of each of the Galvano mirrors 141A and 141B is driven by a drive mechanism (mirror drive mechanisms 241 and 242 shown in FIG. 5 including driving devices such as a motor.

The signal lights LS reflected by the Galvano mirrors 141A and 141B are reflected by reflection mirrors 141C and 141D, thereby traveling in the same direction as having entered into the Galvano mirror 141A.

As described before, the conductive optical fiber 152a runs the optical fiber 152a is arranged facing the lens 142. The signal light LS emitted from this end face 152b travels while expanding its beam diameter toward the lens 142. The light is converged into a parallel light flux by this lens 142. On the contrary, the signal light LS passed through the fundus oculi Ef is converged toward the end face 152b by the lens 142.

[Configuration of OCT Unit]

Next, the configuration of the OCT unit 150 will be described referring to FIG. 3. The OCT unit 150 shown in FIG. 3 has almost the same optical system as the conventional optical image measurement device. The OCT unit 150 comprises an interferometer that splits light emitted from the light source into a reference light and a signal light, and generates interference light by superposing the reference light passed through a reference object and the signal light passed through a measurement object (fundus oculi Ef). The result of detection of the interference light is analyzed, whereby a tomographic image or 3-dimensional image of the fundus oculi Ef is formed.

A low coherence light source 160 is composed of a broadband light source, such as a super luminescent diode (SLD) and a light emitting diode (LED), configured to emit a low coherence light L0. This low coherence light L0 is, for example, a light that has a wavelength of the near-infrared region and has a temporal coherence length of approximately several tens of micrometers. The low coherence light L0 has a longer wavelength than the illumination light (wavelength: about 400 nm through 800 nm) of the retinal camera unit 1A, for example, a wavelength of about 800 nm through 900 nm.

The low coherence light L0 emitted from the low coherence light source 160 is guided to an optical coupler 162 through an optical fiber 161 composed of, for example, a single mode fiber or a PM (Polarization maintaining) fiber. The optical coupler 162 splits this low coherence light L0 into a reference light LR and the signal light LS.

Although the optical coupler 162 acts as both a part for splitting light (i.e., splitter) and a part for superposing lights (i.e., coupler), the optical coupler 162 will be herein referred to as an "optical coupler" idiomatically.

The reference light LR generated by the optical coupler 162 is guided by an optical fiber 163 composed of a single mode fiber or the like, and emitted from the end face of the fiber. The emitted reference light LR is converged into a parallel light flux by a collimator lens 171, passed through a glass block 172 and a density filter 173, and then reflected by a reference mirror 174 (reference object).

The reference light LR reflected by the reference mirror 174 is again passed through the density filter 173 and the glass block 172, and converged to the fiber end face of the optical fiber 163 by the collimator lens 171. The converged reference light LR is guided to the optical coupler 162 through the optical fiber 163.

The glass block 172 and the density filter 173 act as a delaying part for making the optical path lengths (optical distances) of the reference light LR and the signal light LS coincide, and also as a part for making the dispersion characteristics of the reference light LR and the signal light LS coincide.

Further, the reference mirror 174 is configured to be movable along the traveling direction (the direction of the arrow pointing both sides shown in FIG. 3) of the reference light LR. Consequently, the optical path length of the reference light LR according to the axial length of the eye E, etc. is ensured. The reference mirror 174 is moved by a drive mechanism (a reference mirror driving mechanism 243 shown in FIG. 5; described later) including a driving part such as a motor.

On the other hand, the signal light LS generated by the optical coupler 162 is guided to the end of the connection line 152 through an optical fiber 164 composed of a single mode fiber or the like. The conductive optical fiber 152a runs inside the connection line 152. Herein, the optical fiber 164 and the optical fiber 152a may be composed of a single optical fiber, or may be jointly formed by connecting the end faces of the respective fibers. In either case, it is sufficient as far as the optical fiber 164 and 152a are configured to be capable of transferring the signal light LS between the retinal camera unit 1A and the OCT unit 150.

The signal light LS is led through the inside of the connection line 152 and guided to the retinal camera unit 1A. Then, the signal light LS enters into the eye E through the lens 142, the scanning unit 141, the dichroic mirror 134, the imaging lens 126, the relay lens 125, the variable magnifying lens 124, the imaging diaphragm 121, the aperture 112a of the aperture mirror 112, and the objective lens 113. (At this moment, the barrier filters 122 and 123 are retracted from the optical path, respectively.)

The signal light LS having entered the eye E forms an image on the fundus oculi (retina) Ef and is then reflected. At this moment, the signal light LS is not only reflected on the surface of the fundus oculi Ef, but also scattered at the refractive index boundary after reaching the deep area of the fundus oculi Ef. As a result, the signal light LS passed through the fundus oculi Ef is a light containing information reflecting the state of the surface of the fundus oculi Ef and information reflecting the state of backscatter at the refractive index boundary of the deep area tissue of the fundus oculi Ef. This light may be simply referred to as "fundus oculi reflection light of the signal light LS."

The fundus oculi reflection light of the signal light LS travels reversely on the above path to be converged at the end face 152b of the optical fiber 152a, enters into the OCT unit 150 through the optical fiber 152a, and returns to the optical coupler 162 through the optical fiber 164. The optical coupler 162 superimposes the signal light LS and the reference light LR reflected by the reference mirror 174, thereby generating the interference light LC. The generated interference light LC is guided into a spectrometer 180 through an optical fiber 165 composed of a single mode fiber or the like.

Although a Michelson-type interferometer is adopted in the present embodiment, for instance, a Mach Zender type, etc. and any type of interferometer may be adopted appropriately.

The spectrometer 180 comprises a collimator lens 181, a diffraction grating 182, an image-forming lens 183, and a CCD 184. The diffraction grating 182 in the present embodiment is a transmission-type diffraction grating that transmits light; however, needless to say, a reflection-type diffraction grating that reflects light may also be used. Moreover, needless to say, it is also possible to adopt, in place of the CCD 184, other photo-detecting elements.

The interference light LC having entered the spectrometer 180 is split (resolved into spectra) by the diffraction grating 182 after converged into a parallel light flux by the collimator lens 181. The split interference light LC forms an image on the image pick-up surface of the CCD 184 by the image-forming lens 183. The CCD 184 receives the interference light LC and converts to electrical detection signals, and outputs the detection signals to the arithmetic and control unit 200.

[Configuration of Arithmetic and Control Unit]

Next, the configuration of the arithmetic and control unit 200 will be described. This arithmetic and control unit 200 performs a process of analyzing the detection signals inputted from the CCD 184 of the spectrometer 180 of the OCT unit 150, and forming tomographic images of the fundus oculi Ef of the eye E. A technique for this analysis is the same as a conventional technique for the Fourier domain OCT.

Further, the arithmetic and control unit 200 performs a process of forming (image data of) a 2-dimensional image showing the state of the surface (retina) of the fundus oculi Ef, based on the video signals outputted from the imaging devices 10 and 12 of the retinal camera unit 1A.

Furthermore, the arithmetic and control unit 200 executes control of each part of the retinal camera unit 1A and the OCT unit 150.

Control of the retinal camera unit 1A is, for example: control of emission of illumination light by the observation light source 101 or the imaging light source 103; control of insertion/retraction operations of the exciter filters 105 and 106 or the barrier filters 122 and 123 to/from the optical path; control of the operation of a display device such as the LCD 140; control of shift of the illumination diaphragm 110 (control of the diaphragm value); control of the diaphragm value of the imaging diaphragm 121; and control of shift of the variable magnifying lens 124 (control of the magnification). Moreover, the arithmetic and control unit 200 executes control of the rotation operation of the Galvano mirrors 141A and 141B inside the scanning unit 141.

On the other hand, control of the OCT unit 150 is, for example: control of emission of the low coherence light L0 by the low coherence light source 160; control of shift of the reference mirror 174; and control of the accumulated time of the CCD 184.

One example of the hardware configuration of the arithmetic and control unit 200 that acts as described above will be described referring to FIG. 4. The arithmetic and control unit 200 has the same hardware configuration as that of a conventional computer. To be specific, the arithmetic and control unit 200 comprises: a microprocessor 201 (CPU, MPU, etc.), a RAM 202, a ROM 203, a hard disk drive (HDD) 204, a keyboard 205, a mouse 206, a display 207, an image forming board 208, and a communication interface (I/F) 209. These parts are connected via a bus 200a.

The microprocessor 201 executes operations characteristic to the present embodiment, by loading a control program 204a stored in the hard disk drive 204, onto the RAM 202.

Further, the microprocessor 201 executes control of each part of the device described above, various arithmetic processes, etc. Moreover, the microprocessor 201 executes control of each part of the device corresponding to an operation signal from the keyboard 205 or the mouse 206, control of a display process by the display 207, and control of a transmission/reception process of various data, control signals and so on by the communication interface 209.

Various kinds of information, including patient information such as a patient name and a patient ID and image data of a fundus oculi image, are stored in the hard disk drive 204. As the patient information, information (reference mirror position information) indicating the position of the reference mirror 174 during image measurement of a fundus oculi conducted by the OCT unit 150, and information (scan position information) indicating the scan positions such as scan start position, scan end position, or scan intervals of signal lights.

The keyboard 205, the mouse 206 and the display 207 are used as user interfaces in the fundus oculi observation device 1. The keyboard 205 is used as, for example, a device for typing letters, figures, etc. The mouse 206 is used as a device for performing various input operations to the display screen of the display 207.

Further, the display 207 is any display device composed of an LCD, a CRT (Cathode Ray Tube) display or the like. The display 207 displays various images of the fundus oculi Ef formed by the fundus oculi observation device 1, and displays various screens such as an operation screen and a set-up screen.

The user interface of the fundus oculi observation device 1 is not limited to the above configuration, and may be configured by using any user interface having a function of displaying and outputting various information, and a function of inputting various information and operating the device, such as a track ball, a control lever, a touch panel type of LCD, and a control panel for ophthalmology examinations.

The image forming board 208 is a dedicated electronic circuit for a process of forming (image data of) images of the fundus oculi Ef of the eye E. This image forming board 208 is provided with a fundus oculi image forming board 208a and an OCT image forming board 208b. The fundus oculi image forming board 208*a* is a dedicated electronic circuit that operates to form image data of fundus oculi images based on the video signals from the imaging device 10 and the imaging device 12 of the retinal camera unit 1A. Further, the OCT image forming board 208*b* is a dedicated electronic circuit that operates to form image data of fundus oculi images (tomographic images) of the fundus oculi Ef, based on the detection signals from the CCD 184 of the spectrometer 180 in the OCT unit 150. By providing the image forming board 208, it is possible to increase the processing speed for forming image data of fundus oculi images and tomographic images.

The communication interface 209 performs a process of sending control signals from the microprocessor 201, to the retinal camera unit 1A or the OCT unit 150. Moreover, the communication interface 209 performs a process of receiving video signals from the imaging devices 10 and 12 of the retinal camera unit 1A and detection signals from the CCD 184 of the OCT unit 150, and inputting the signals to the image forming board 208. At this time, the communication interface 209 operates to input the video signals from the imaging devices 10 and 12, to the fundus oculi image forming board 208*a*, and input the detection signal from the CCD 184, to the OCT image forming board 208*b*.

Further, in a case where the arithmetic and control unit 200 is connected to a network such as a LAN (Local Area Network) and the Internet, it is possible to configure so as to be capable of data communication via the network, by providing the communication interface 209 with a network adapter like a LAN card or communication equipment like a modem. In this case, it is possible to mount a server accommodating the control program 204*a*, and also configure the arithmetic and control unit 200 as a client terminal of the server.

Furthermore, it is possible to configure so as to store any of the various kinds of information (described before) stored in the hard disk drive 204, into a server on a network or into a database.

[Configuration of Control System]

The configuration of the control system of the fundus oculi observation device 1 having the aforementioned configuration will be described referring to FIG. 5. FIG. 5 shows a part relating to the operation and process relating to the present invention particularly selected from among the components of the fundus oculi observation device 1.

The control system of the fundus oculi observation device 1 is configured mainly having a controller 210 of the arithmetic and control unit 200. The controller 210 comprises the microprocessor 201, the RAM202, the ROM203, the hard disk drive 204 (control program 204*a*), and the communication interface 209.

The controller 210 executes the aforementioned controlling processes through the microprocessor 201 operating based on the control program 204*a*. In specific, the controller 210 controls the mirror drive mechanisms 241 and 242 of the retinal camera unit 1A, respectively, thereby causing the Galvano mirrors 141A and 141B to operate independently.

Further, the controller 210 executes control for causing the display 207 of the user interface 240 to display two types of images captured by the fundus oculi observation device 1: that is, a 2-dimensional image (fundus oculi image Ef') of the surface of the fundus oculi Ef obtained by the retinal camera unit 1A, and an image of the fundus oculi Ef formed based on the detection signals obtained by the OCT unit 150. These images may be displayed on the display 207 separately, or may be displayed side by side simultaneously.

An image forming part 220 performs a process of forming a fundus oculi image based on video signals from the imaging devices 10 and 12 of the retinal camera unit 1A, and a process of forming a fundus oculi image based on detection signals from the CCD 184 of the OCT unit 150. The imaging forming part 220 comprises the imaging forming board 208.

The image processor 230 applies various image processing to a fundus oculi image formed by the image forming part 220. For example, the image processor 230 executes a process of forming a 3-dimensional image of the fundus oculi Ef based on the tomographic images of the fundus oculi Ef' based on the detection signals from the OCT unit 150, and various correction processes such as brightness correction and dispersion correction of the images.

Further, the image processor 230 executes a characteristic process in the present invention (described later): forms one tomographic image by calculating based on tomographic images of two or more cross sections. The image processor 230 is to function as one example of the image processor of the present invention.

The user interface (UI) 240 is equipped with input devices (operation devices) such as a keyboard 205 and a mouse 206, and a display device such as a display 207.

The image storage 250 stores the (image data of) images formed by the image forming part 220 or the image processor 230. The image storage 250 includes a storage device such as a hard disk drive 204. The arithmetic and control device 200 is equivalent to one example of the image processing device of the present invention, and the image storage 250 functions as one example of the storage of the present invention.

Herein, a mode of control of scan of the signal light LS by the controller 210, and a mode of a process to a detection signal from the OCT unit 150 by the image forming part 220 and the image processor 230 will be respectively described. An explanation regarding the process by the image forming part 220, etc., to the video signal from the retinal camera unit 1A will be omitted because it is the same as the conventional process.

[Signal Light Scanning]

Scan of the signal light LS is performed by changing the directions of the reflecting surfaces of the Galvano mirrors 141A and 141B of the scanning unit 141 in the retinal camera unit 1A. By controlling the mirror drive mechanisms 241 and 242 respectively to change the directions of the reflecting surfaces of the Galvano mirrors 141A and 141B respectively, the controller 210 scans the application position of the signal light LS on the fundus oculi Ef.

When the facing direction of the reflecting surface of the Galvano mirror 141A is changed, the signal light LS is scanned in the horizontal direction (x-direction in FIG. 1) on the fundus oculi Ef. On the other hand, when the facing direction of the reflecting surface of the Galvano mirror 141B is changed, the signal light LS is scanned in the vertical direction (y-direction in FIG. 1) on the fundus oculi Ef. Further, by changing the facing directions of the reflecting surfaces of both the Galvano mirrors 141A and 141B simultaneously, it is possible to scan the signal light LS in the composed direction of the x-direction and y-direction. That is, by controlling these two Galvano mirrors 141A and 141B, it is possible to scan the signal light LS in any direction on the x-y plane.

Figure 6A:
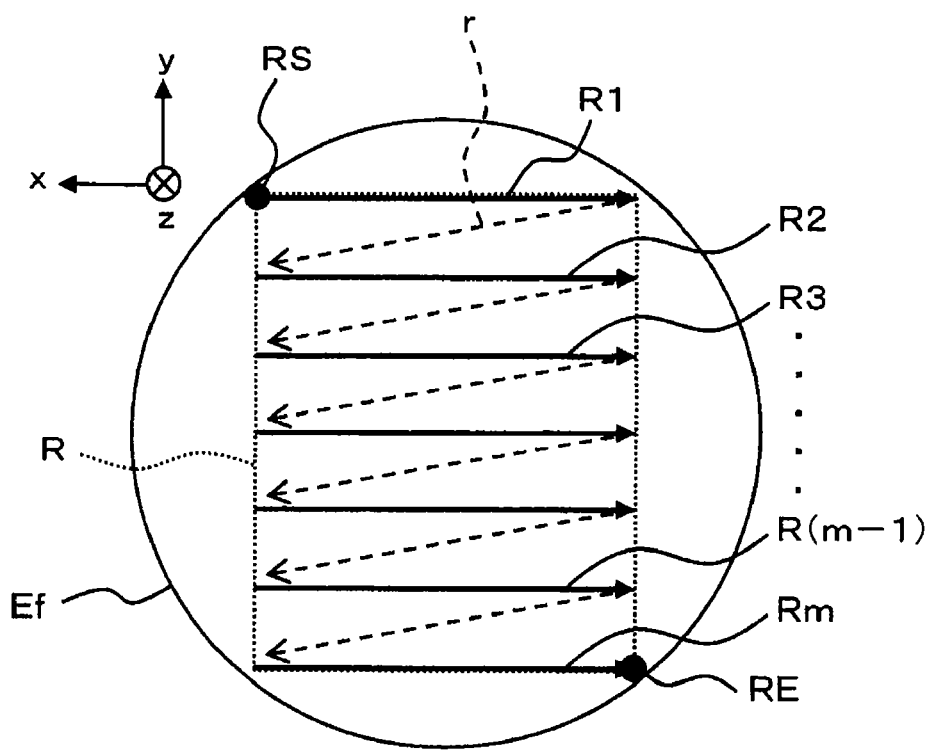
FIGS. 6A and 6B are schematic diagrams showing an example of a scanning mode of signal light in the preferred embodiment of the fundus oculi observation device comprising the optical image measurement device according to the present invention.
Figure 6B:
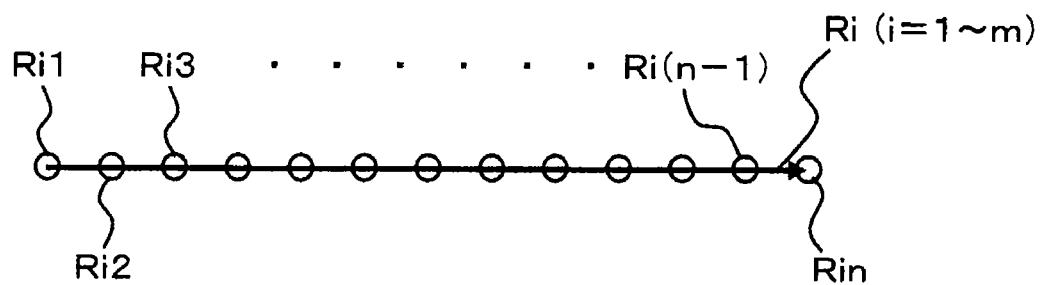

FIGS. 6A and 6B show an example of a mode of scan of the signal light LS for forming an image of the fundus oculi Ef. FIG. 6A shows an example of a mode of scan of the signal light LS, when the fundus oculi Ef is seen from a direction that the signal light LS enters the eye E (that is, seen from −z side toward +z side in FIG. 1). Further, FIG. 6B shows one example of the feature of arrangement of scanning points (positions at which image measurement is carried out) on each scanning line on the fundus oculi Ef.

As shown in FIG. 6A, the signal light LS is scanned within a rectangular-shaped scanning region R that has been preset. Within this scanning region R, a plurality of (m number of) scanning lines R1 through Rm are set in the x-direction. When the signal light LS is scanned along the respective scanning lines Ri (i=1 through m), detection signals of the interference light LC are generated.

Herein, a direction of each scanning line Ri will be referred to as the "main scanning direction" and a direction orthogonal thereto will be referred to as the "sub-scanning direction". Accordingly, scanning of the signal light LS in the main scanning direction is performed by changing the facing direction of the reflecting surface of the Galvano mirror 141A, and scanning in the sub-scanning direction is performed by changing the facing direction of the reflecting surface of the Galvano mirror 141B.

On each scanning line Ri, as shown in FIG. 6B, a plurality of (n number of) scanning points Ri1 through Rin are preset.

In order to execute the scanning shown in FIGS. 6A and 6B, the controller 210 firstly controls the Galvano mirrors 141A and 141B to set the target of the signal light LS entering into the fundus oculi Ef to a scan start position RS (scanning point R11) on the first scanning line R1. Subsequently, the controller 210 controls the low coherence light source 160 to flush the low coherence light L0, thereby making the signal light LS enter the scan start position RS. The CCD 184 receives the interference light LC based on the fundus oculi reflection light of this signal light LS at the scan start position RS, and outputs the detection signal to the controller 210.

Next, the controller 210 controls the Galvano mirror 141A to scan the signal light LS in the main scanning direction and set the incident target of the signal light LS to a scanning point R12, and makes the low coherence light L0 flushed to make the signal light LS enter into the scanning point R12. The CCD 184 receives the interference light LC based on the fundus oculi reflection light of this signal light LS at the scanning point R12, and then outputs the detection signal to the controller 210.

Likewise, the controller 210 obtains detection signals outputted from the CCD 184 in response to the interference light LC for each scanning point, by flushing the low coherence light L0 at each scanning point while shifting the incident target of the signal light LS from scanning point R13 to R14, - - - , R1 (n−1), and R1n in order.

When the measurement at the last scanning point R1n of the first scanning line R1 is finished, the controller 210 controls the Galvano mirrors 141A and 141B simultaneously to shift the incident target of the signal light LS to the first scanning point R21 of the second scanning line R2 following a line switching scan r. Then, by conducting the previously described measurement on each scanning point R2j (j=1 through n) of this second scanning line R2, detection signals corresponding to the respective scanning points R2j are obtained.

Likewise, the measurement is conducted for each of the third scanning line R3, - - - , the m−1th scanning line R(m−1), the mth scanning line Rm to obtain the detection signals corresponding to the respective scanning points. Symbol RE on a scanning line Rm is a scan end position corresponding to a scanning point Rmn.

As a result, the controller 210 obtains m×n number of detection signals corresponding to m×n number of scanning points Rij (i=1 through m, j=1 through n) within the scanning region R. Hereinafter, a detection signal corresponding to the scanning point Rij may be represented by Dij.

Such interlocking control of the shift of scanning points and the emission of the low coherence light L0 can be realized by synchronizing, for instance, timing for transmission of control signals to the mirror drive mechanisms 241 and 242 and timing for transmission of control signals (output request signals) to the low coherence light source 160.

As described above, when each of the Galvano mirrors 141A and 141 B is operated, the controller 210 stores the position of each scanning line Ri and the position of each scanning point Rij (coordinates on the x-y coordinate system) as information representing the content of the operation. This stored content (scan position information) is used in an image forming process as in conventional one.

[Image Processing]

Next, an example of a process on OCT images (tomography images of the fundus oculi Ef) by the image forming part 220 and the image processor 230 will be described.

The image forming part 220 executes the formation process of tomographic images of the fundus oculi Ef along each scanning line Ri (main scanning direction). Further, the image processor 230 executes the formation process of a 3-dimensional image of the fundus oculi Ef based on these tomographic images formed by the image forming part 220, etc.

The formation process of a tomographic image by the image forming part 220, as in the conventionally one, includes a 2-step arithmetic process. In the first step of the arithmetic process, based on a detection signal Dij corresponding to each scanning point Rij, an image in the depthwise direction (z-direction in FIG. 1) of the fundus oculi Ef at the scanning point Rij is formed.

Figure 7:
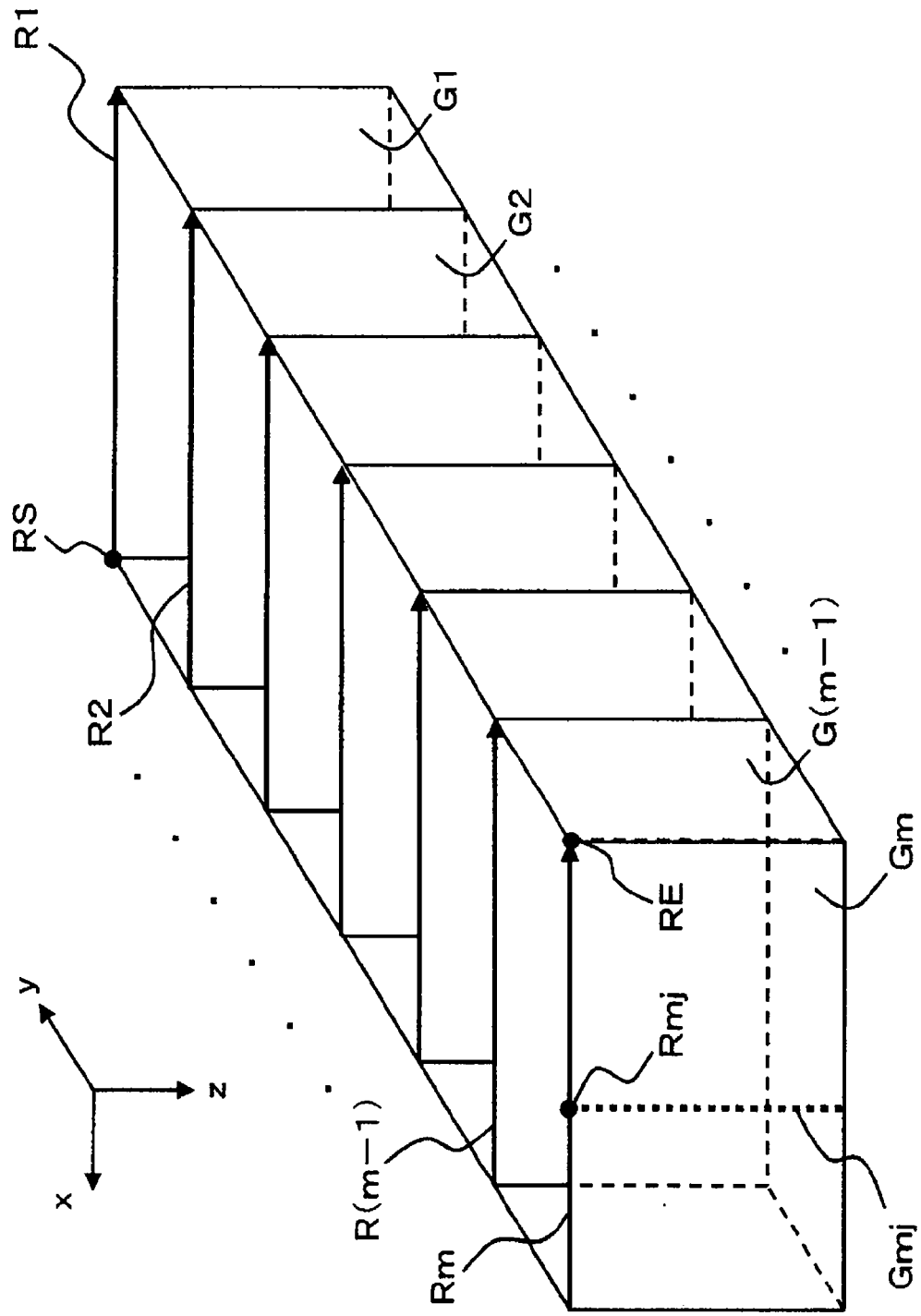
FIG. 7 is a schematic diagram showing an example of a scanning mode of signal light and a mode of a tomographic image formed along each scanning line in the preferred embodiment of the fundus oculi observation device comprising the optical image measurement device according to the present invention.

FIG. 7 shows a mode of a tomographic image formed by the image forming part 220. In the second step of the arithmetic process, on each scanning line Ri, based on the images in the depth-wise direction at the n number of scanning points Ri1 through Rin, a tomographic image G1 of the fundus oculi Ef along the scanning line Ri is formed. Then, the image forming part 220 determines the arrangement and the distance of the scanning points Ri1 through Rin referring to the positional information (scan position information described before) of the scanning points Ri1 through Rin, and forms a tomographic image Gi along this scanning line Ri. Through the above process, m number of tomographic images (a group of tomographic images) G1 through Gm at different positions in the sub-scanning direction (y-direction) are obtained.

Here, the formation process of a 3-dimensional image of the fundus oculi Ef by the image processor 230 will be explained. A 3-dimensional image of the fundus oculi Ef is formed based on the m number of tomographic images obtained through the above arithmetic process. The image processor 230 forms a 3-dimensional image of the fundus oculi Ef by performing a known interpolating process to interpolate an image between the adjacent tomographic images Gi and G(i+1).

Here, the image processor 230 determines the arrangement and the distance of each scanning line Ri while referring to the positional information of each scanning line Ri to form this 3-dimensional image. For this 3-dimensional image, a 3-dimensional coordinate system (x,y,z) is set, based on the positional information (the scan position information) of each scanning point Rij and the z-coordinate in the depth-wise image.

Furthermore, based on this 3-dimensional image, the image processor 230 can form a tomographic image of the fundus oculi Ef at a cross-section in any direction other than the main scanning direction (x-direction). Once the cross-section is designated, the image processor 230 determines the position of each scanning point (and/or an interpolated depthwise image) on this designated cross-section, and extracts a depth-wise image at each determined position (and/or an interpolated depth-wise image), thereby forming a tomographic image of the fundus oculi Ef at the designated cross-section by arranging plural extracted depth-wise images.

Furthermore, an image Gmj shown in FIG. 7 represents an image in the depth-wise direction (z-direction) at the scanning point Rmj on the scanning line Rm. A depth-wise image at each scanning point Rij on the scanning line Ri formed by the first-step arithmetic process is represented as "image Gij."

[Operation]

Figure 8:
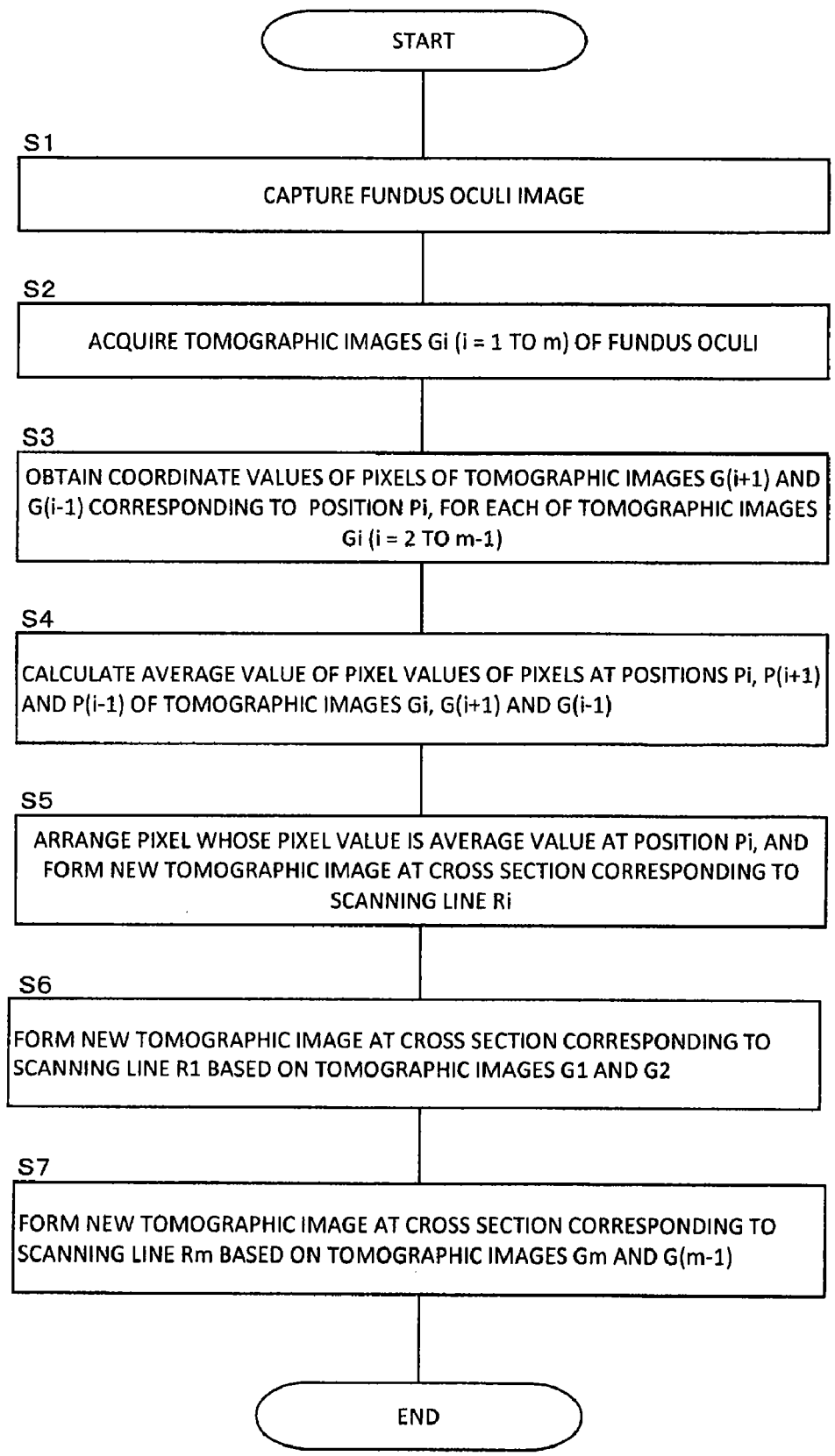
FIG. 8 is a flowchart showing an operation example at the time execution of optical image measurement in the preferred embodiment of the fundus oculi observation device comprising the optical image measurement device according to the present invention.

An operation of the fundus oculi observation device 1 having the aforementioned configuration will be described. A flowchart shown in FIG. 8 represents an example of the operation of the fundus oculi observation device 1.

First, the fundus oculi observation device 1 captures a 2-dimensional image (fundus oculi image Ef) of the surface of the fundus oculi Ef of the eye E (S1), and obtains tomographic images Gi (i=1 to m) of the fundus oculi Ef (S2).

The controller 210 causes the image storage 250 to store (the image data of) the fundus oculi image Ef and (the image data of) the tomographic images Gi. In the case of executing only the process relating to the present invention, it is not necessary to capture the fundus oculi image Ef in Step S1.

The controller 210 reads out the tomographic images G1 to Gm from the image storage 250, and sends the images to the image processor 230. Each of the tomographic images Gi is a tomographic image having a cross section extending in the depth-wise direction (+z direction) of the fundus oculi Ef from a scanning line Ri. The cross section of the tomographic image Gi may be referred as the "cross section corresponding to the scanning line Ri" hereinafter.

The image processor 230 executes an arithmetic operation based on the tomographic image Gi (i=2 to m−1), tomographic images G (i+1) and tomographic images G (i−1), thereby forming a new tomographic image at the cross section corresponding to the scanning line Ri (S3 to S5). Below, this process will be described in detail.

Figure 9:
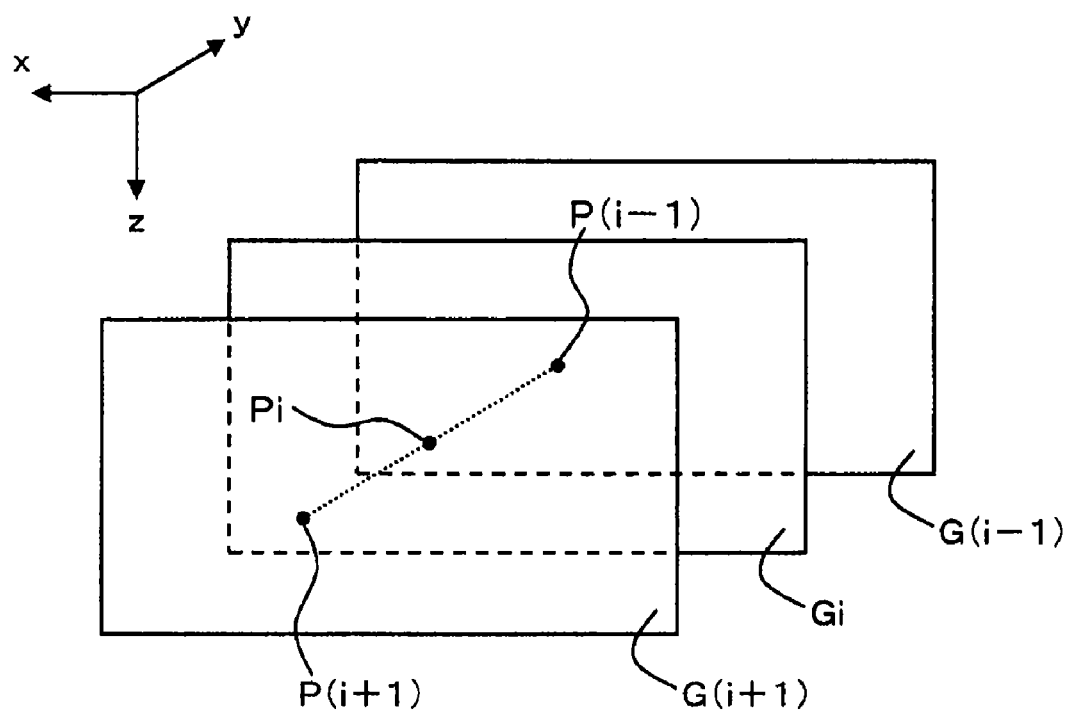
FIG. 9 is a schematic explanation view for explaining the preferred embodiment of the fundus oculi observation device comprising the optical image measurement device according to the present invention.

The tomographic image Gi has the cross section corresponding to the scanning line Ri. The tomographic images G (i+1) and G (i−1) respectively have a cross section corresponding to a scanning line R (i+1) and a cross section corresponding to a scanning line R (i−1), which are adjacent to the scanning line Ri. Therefore, the cross section corresponding to the scanning line R (i+1) and the cross section corresponding to the scanning line R (i−1) are adjacent to the cross section corresponding to the scanning line Ri, respectively. Moreover, the cross sections corresponding to the scanning lines Ri, R (i+1) and R (i−1) are arranged in the y direction as shown in FIG. 9.

In relation to the aforementioned new tomographic image, an example of the process for determining the pixel value of a pixel at an optional position Pi=(xi, yi, zi) in the cross section corresponding to the scanning line Ri will be described. By thus determining the pixel value of the pixel at the arbitrary position Pi, it is possible to form the aforementioned new tomographic image.

First, the image processor 230 obtains the coordinate values of pixels of the tomographic images G (i+1) and G (i−1) corresponding to the position Pi (S3).

For this purpose, the image processor 230 obtains the equation of a straight line that is through the position Pi and parallel to the y direction (a dotted part in FIG. 9), and further obtains the coordinates of the position P (i+1) where the straight line intersects with the tomographic image G (i+1). The coordinates of the position P (i+1) are (xi, y (i+1), zi), which are the coordinate values of the pixel of the tomographic image P (i+1) corresponding to the position Pi. Likewise, the coordinate values of the position P (i−1) where the straight line intersects with the tomographic image G (i−1) are (xi, y (i−1), zi), which are coordinate values of the tomographic image P (i−1) corresponding to the position Pi.

Here, yi, y (i+1) and y (i−1) are y coordinate values of the scanning lines Ri, R (i+1) and R (i−1), respectively, shown in FIG. 6A. Further, the y coordinate values of the respective scanning lines Ri, R (i+1) and R (i−1) can be acquired from the aforementioned scan position information. Therefore, instead of using a straight line as described above, it is possible to use the y coordinate values y(i+1) and y(i−1) of the scanning lines R(i+1) and R(i−1), thereby obtaining the coordinate values (xi, y(i+1), zi), (xi, y(i−1), zi) of the pixels of the tomographic images G(i+1) and G(i−1) corresponding to the position Pi.

Next, the image processor 230 calculates the average value of the pixel value of the pixel at the position Pi of the tomographic image Gi, the pixel value of the pixel at the position P(i+1) of the tomographic image G(i+1) and the pixel value of the pixel at the position P(i−1) of the tomographic image G(i−1) (S4).

Here, it is possible to properly use any arithmetic method for obtaining one value by executing a statistical calculation for a plurality of values (may be referred as "average value etc."), such as the median, instead of the average value of these pixel values.

After calculating the aforementioned average value etc. for each of the positions Pi, the image processor 230 arranges a pixel having the average value etc. as a pixel value, at each of the positions Pi, thereby forming a tomographic image (S5). This tomographic image is a targeted tomographic image, that is, a new tomographic image at the cross section corresponding to the scanning line Ri.

The image processor 230 executes the process of Steps S3 to S5 for each of the tomographic images Gi (i=2 to m−1).

Furthermore, the image processor 230 executes the similar process as described above by using tomographic images G1 and G2 to thereby form a new tomographic image at a cross section corresponding to a scanning line R1 (S6), and executes the similar process as described above by using tomographic images Gm and G(m−1) to thereby form a new tomographic image at a cross section corresponding to a scanning line Rm (S7).

The controller 210 causes the image storage 250 to store m number of new tomographic images that have been formed in Steps S5 to S7. Further, the image processor 230 can form a 3-dimensional image of the fundus oculi Ef based on the new tomographic images that have been formed in Steps S5 to S7 if necessary. Moreover, the image processor 230 can form a tomographic image at any cross section of the fundus oculi Ef if necessary, based on the 3-dimensional image. This is the end of the explanation for the operation of the fundus oculi observation device 1 relating to the present embodiment.

[Actions and Advantageous Effects]

The actions and advantageous effects of the fundus oculi observation device 1 (optical image measurement device) relating to the present embodiment that operates as described above will be explained.

This fundus oculi observation device 1 acts so as to, for a cross section corresponding to each scanning line Ri, execute an arithmetic operation based on a tomographic image Gi at this cross section, a tomographic image G(i+1) at a cross section corresponding to a scanning line R(i+1) and a tomographic image G(i−1) at a cross section corresponding to a scanning line R(i−1), thereby forming a new tomographic image at the cross section corresponding to the scanning line Ri.

This new tomographic image is formed by using the result of measurement at a single cross section (the cross section corresponding to the scanning line Ri) and the result of measurement at other cross sections (the cross sections corresponding to the scanning lines R(i+1) and R(i−1)).

Therefore, according to the fundus oculi observation device 1, it is possible to increase the image quality of a tomographic image to be formed, compared with the conventional configuration of forming a tomographic image based on only the result of measurement at a single cross section. Further, by forming a 3-dimensional image based on these new tomographic images, it is possible to acquire a 3-dimensional image with higher image quality than conventional. Moreover, by forming a tomographic image at an arbitrary cross section based on this 3-dimensional image, it is possible to acquire a tomographic image with higher image quality than conventional.

Further, the fundus oculi observation device 1 is configured to, in the process for forming a new tomographic image at a cross section corresponding to a scanning line Ri, refer to tomographic images at cross sections corresponding to scanning lines R(i+1) and R(i−1), which are adjacent to the cross section corresponding to the scanning line Ri, so that it is possible to increase the image quality of a new tomographic image to be formed.

Moreover, the fundus oculi observation device 1 is configured to calculate the average value etc. of the pixel value of the pixel of the tomographic image Gi at a position Pi and the pixel values of the pixels of the tomographic images G(i+1) and G(i−1) at positions P(i+1) and P(i−1) corresponding to the position Pi, and form a new tomographic image having the average value etc. as the pixel value of the pixels at the position Pi. By executing such a statistical calculation to obtain the pixel value of each pixel and form a new tomographic image, it is possible to increase the image quality.

[Modification]

The configuration described in detail above is merely an example for favorably implementing the optical image measurement device relating to the present invention. Therefore, it is possible to properly apply any modification within the scope of the present invention. Below, various types of modifications of the optical image measurement device according to the present invention will be described.

In the above embodiment, a new tomographic image is formed for a cross section of each tomographic image Gi (i=1 to m) acquired in Step S2. However, it is also possible to form new tomographic images for only an arbitrary number of cross sections among the cross sections of the tomographic image Gi.

In the above embodiment, for a cross section of each tomographic image Gi (i=2 to m−1), a new tomographic image is formed with tomographic images G(i+1) and G(i−1) located on both sides of the tomographic image Gi. However, it is also possible to form a new tomographic image with tomographic images G(i+1) . . . G(i+p), G(i−1) . . . G(i−q) at an arbitrary number of cross sections that are adjacent to the cross section of the tomographic image Gi (herein, $p \geq 0$, $q \geq 0$, $1 \leq p+q \leq m-1$).

"To be adjacent to a cross section of a tomographic image Gi" means "to be included in the range of a distance from the cross section or of the number of cross sections, which is previously set as tomographic images of other cross sections used in the process of forming a new tomographic image at the cross section.

In a case where the range of the distance (for example, $0 < \text{dist} \leq D$) is previously set and an interval of adjacent cross sections is d, the image processor 230 forms a new tomographic image at the cross section by involving tomographic images of [D÷d] number on both sides (or one side) of the cross section (herein, [•] is the Gauss symbol).

Further, in a case where the range of the number of cross sections $M \geq 1$ is previously set, the image processor 230 forms a new tomographic image at the cross section by involving M number of tomographic images on both sides (or one side) of the cross section.

Moreover, also for each of the cross sections of the tomographic images G1 and Gm, it is possible to form a new tomographic image by involving tomographic images at any number of cross sections adjacent to the cross section.

In the embodiment described before, tomographic images at a plurality of cross sections arranged so as to be parallel to each other have been described. However, the pattern of the cross sections is optional.

Figure 10:
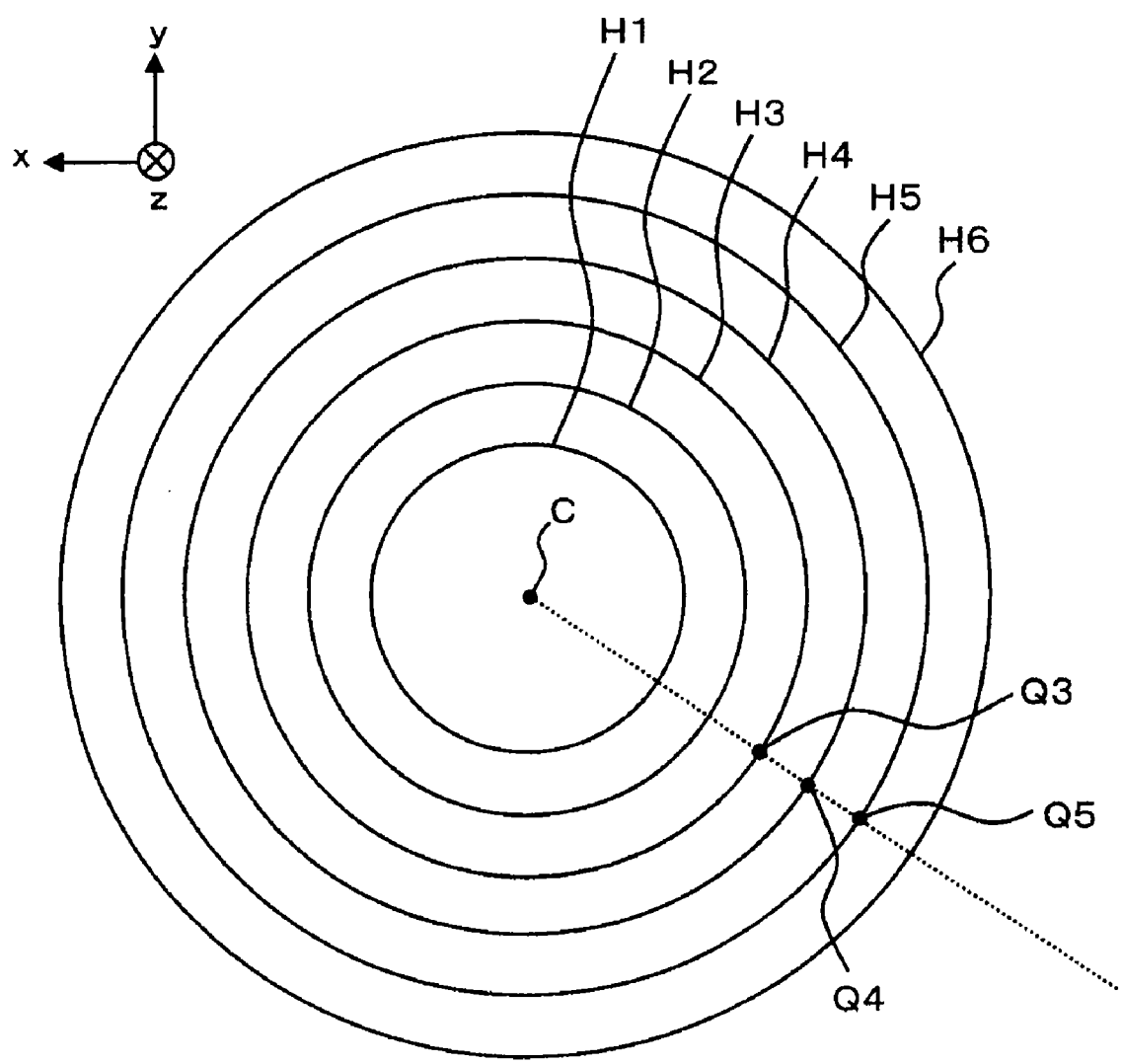
FIG. 10 is a schematic explanation view for explaining a modification of the preferred embodiment of the fundus oculi observation device comprising the optical image measurement device according to the present invention.

For example, as shown in FIG. 10, there is a case of acquiring tomographic images H1 to H6 at a plurality of (six) cross sections arranged concentrically. The process of forming a new tomographic image at a cross section of a tomographic image H4 in this case will be described. Here, symbol C represents a center position (referred to as a scan center) of circular scan of a signal light LS for acquiring the tomographic images H1 to H6 at the cross sections arranged concentrically. The number of cross sections arranged concentrically is generally numerous (several dozens to several hundreds).

First, for an arbitrary position Q4 of the cross section of the tomographic image H4, the image processor 230 obtains the equation of a straight line connecting the position Q4 and the scan center C (a dotted line part in FIG. 10). Next, the image processor 230 obtains positions Q3 and Q5 where the straight line crosses the cross sections of tomographic images H3 and H5, respectively. The positions Q3 and Q5 are positions of the cross sections of the tomographic images H3 and H5 corresponding to the position Q4 of the cross section of the tomographic image H4. Furthermore, the image processor 230 calculates an average value etc. of the pixel value of a pixel of the position Q4, the pixel value of a pixel of the position Q3 and the pixel value of a pixel a of the position Q5. By executing this process for each position Q4 of the cross section of the tomographic image H4, it is possible to form a new tomographic image at the cross section.

Next, acquisition of a tomographic image at a spirally-shaped cross section will be described. Although the spirally-shaped cross section is a single cross section, a cross section for one rotation around a spiral center is here defined as one cross section. Thus, it is possible to form a new tomographic image at any position of the spirally-shaped cross section, in the same manner as in the case of the cross sections arranged concentrically.

Figure 11:
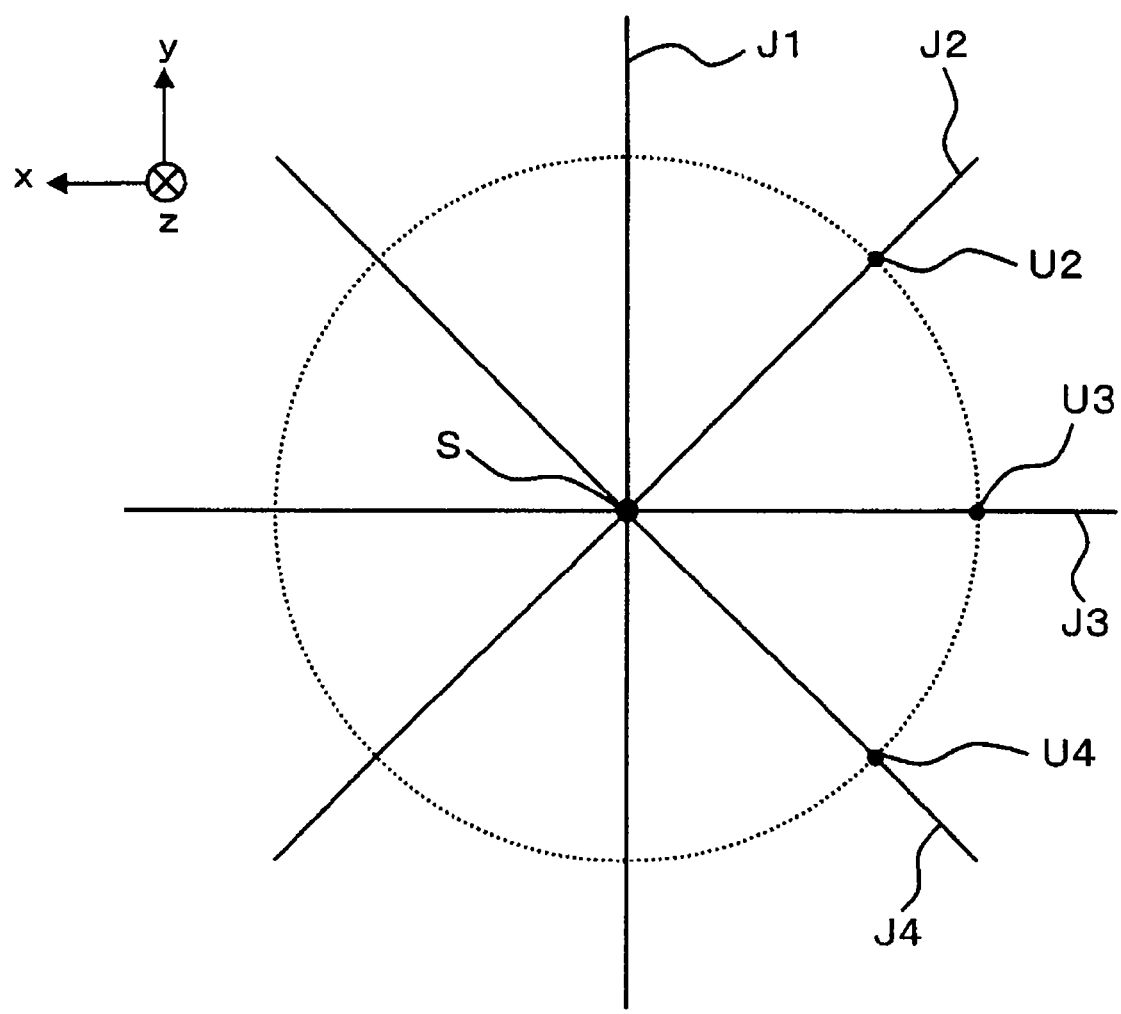
FIG. 11 is a schematic explanation view for explaining a modification of the preferred embodiment of the fundus oculi observation device comprising the optical image measurement device according to the present invention.

Next, acquisition of tomographic images at a plurality of radially-arranged cross sections will be described. FIG. 11 shows tomographic images J1 to J4 of four cross sections arranged radially. Herein, symbol S represents the intersection of these cross sections. The number of radially-arranged cross sections is generally numerous (several dozens to several hundreds).

First, for an optional position U3 of the cross section of a tomographic image J3, the image processor 230 obtains the equation of a circle that takes the cross-section intersection S as the center thereof and passes through the position U3 (a dotted line part in FIG. 11). Next, the image processor 230 obtains positions U2 and U4 where this circle crosses the cross sections of the tomographic images J2 and J4, respectively. The positions U2 and U4 are positions in the cross sections of the tomographic images J2 and J4 that correspond to the position U3 in the cross section of the tomographic image J3. Furthermore, the image processor 230 calculates an average value etc. of the pixel value of a pixel of the position U3, the pixel value of a pixel of the position U2 and the pixel value of a pixel of the position U4. By executing this process for each position U3 in the cross section of the tomographic image J3, it is possible to form a new tomographic image at the cross section.

It is possible to apply this process to any pattern of cross sections in which the cross sections cross each other, other than the radially-arranged cross sections.

In the above embodiment, the process of forming a fundus oculi image is executed by the image forming part 220 (image forming board 208), and various types of control process are executed by the controller 210 (microprocessor 201 or the like). However, it is possible to configure so as to execute both the processes by using one or more computer(s).

In the above embodiment, a fundus oculi observation device having a function of a retinal camera and a function of an optical image measurement device has been described. However, it is also possible to apply the configuration of the present invention to a device having other fundus oculi observation functions such as a function of a slit lamp (slit lamp microscopic device) and a function of an optical image measurement device.

Further, the configuration according to the present invention is applicable to not only the complex devices described above but also a normal optical image measurement device.

For example, it is possible to apply the configuration according to the present invention that automatically sets the position of a reference object, to any optical image measurement device configured to determine the depth-wise position in a funds oculi based on the position of a reference object, such as the optical image measurement device disclosed in Japanese Unexamined Patent Application Publication JP-A 2005-241464 by the present inventors.

Further, it is possible to apply the configuration according to the present invention that automatically sets a scan position of a signal light, to any optical image measurement device having a configuration that scans with a signal light by using a Galvano mirror or the like, such as the optical image measurement device disclosed in Japanese Unexamined Patent Application Publication JP-A No. 2007-130403 by the present inventors.

Moreover, in the above embodiment, tomographic images of a fundus oculi are formed. However, the "measurement object" in the present invention may be any object from which tomographic images can be acquired by an optical image measurement device, such as any living organs and industrial products.

For execution of the process relating to the present invention with high accuracy, the accuracy in positional relationship between one tomographic image to become a correction subject and another tomographic image to be referred in the correction process is important (ref. FIG. 9). Below, an example of this position-matching process will be described.

As a first example, a method using an "accumulated image" described in Japanese Unexamined Patent Application Publications JP-A 2007-130403, JP-A 2007-252692, JP-A 2007-325831, etc. will be described.

An accumulated image is an image generated by accumulating tomographic images in the depth-wise direction. Here, "to accumulate in the depth-wise direction" means an arithmetic process of summing up (projecting), in the depth-wise direction, luminance values (pixel values) at the respective depth positions of images Gij of the respective depth-wise directions included in tomographic images. A dotted image acquired by accumulating the images Gij of the respective depth-wise directions has a luminance value obtained by, in the depth-wise direction, summing up the luminance values at the respective z positions of the images Gij in the depth-wise direction.

The process of forming an accumulated image is executed by the image processor 230. Specifically, the image processor 230 accumulates the respective m×n number of images Gij in the depth-wise direction, thereby forming an accumulated image composed of m×n number of dotted images that are 2-dimensionally distributed in a scanning region R. This accumulated image becomes an image representing the form of the surface of the fundus oculi Ef, as well as the fundus oculi image Ef' (2-dimensional image of the fundus oculi surface) in the scanning region R.

The image processor 230 matches the positions of the fundus oculi image Ef' and the accumulated image. This process can be realized by specifying a blood vessel region within the fundus oculi image Ef' and a blood vessel region within the accumulated image and executing position-matching of the blood vessel regions, as in the above document, for example. Consequently, the positional relation (positional relation in the x-y direction) of m number of tomographic images G1 to Gm can be corrected with reference to the fundus oculi image Ef'.

For the tomographic images G1 to Gm in which the positional relation has been thus corrected, the image processor 230 obtains the coordinate values of pixels P(i+1) and P(i−1) of tomographic images G(i+1) and G(i−1), which correspond to an arbitrary pixel (position) Pi of each tomographic image Gi (ref. to Step 3 in FIG. 8), and further executes the process of Steps 4 and after shown in FIG. 8.

According to this modification, it is possible to enhance the accuracy in positional relation in the x-y direction between one tomographic image Gi to become a subject to be corrected and other tomographic images G(i+1) and G(i−1) referred in the correction process, and it becomes possible to execute the process related to the present invention with high accuracy.

Likewise, it is also possible to enhance the accuracy in positional relation in the depth-wise direction by correcting the positional relation in the depth-wise direction (z direction) of the tomographic images G1 to Gm. Herein, the process of correcting the positional relation in the depth-wise direction can be conducted by, for example, adjusting the z position of a tomographic image Gi so as to match the depth position of a layer that is represented by the tomographic image Gi. This concludes the explanation of the first example.

Next, a second example is described. In the second example, a method of enhancing the accuracy in positional relation between one tomographic image to be a correction subject and other tomographic images referred in the correction process, by detecting movements of an eye referring a fundus oculi image Ef'.

The fundus oculi image Ef' used in the present example is, for example, a moving image for fundus oculi observation acquired with infrared illumination light. It is preferable if the frame rate of the moving image is synchronized with the scan by a signal light LS (e.g., the switching timing of the frames of the moving image is synchronized with the switching timing of the scanning line Ri). More specifically, it is preferred to acquire one frame every time one tomographic image Gi is acquired (that is, every time each scanning line Ri is scanned). Thus, it is possible to associate one frame with each of the tomographic images Gi. Such synchronizing processes are executed by the controller 210.

The image processor 230 specifies a characteristic image region (characteristic region) from an image within each frame thus acquired. The characteristic region can include, for example, an image region corresponding to the peripheral part of an optic disk, an image region corresponding to the center position of an optic disk, an image region corresponding to a macula part, an image region corresponding to a branching position or an end part of a blood vessel, and so on. The process of specifying these characteristic regions can be executed by, for example, employing any known image-processing technique such as a threshold process for pixel values and a pattern recognition process. It is to be noted that the same characteristic region is specified for the respective frames.

Subsequently, the image processor 230 obtains the position of the specified characteristic region within a frame for the respective frames. Furthermore, based on these positions, the image processor 230 obtains time-series changes of the position of the characteristic region in the moving image. Consequently, for example, a displacement of the characteristic region within each of the frames with respect to the position (reference position) of the characteristic region in the first frame (presumed to be corresponding to the first scanning line R1) can be observed. The displacement is a displacement in the x-y direction.

Based on the displacement of the characteristic region within each of the frames, the image processor 230 corrects the position in the x-y direction of a tomographic image Gi that has been associated with the frame. The correction process is conducted by changing the position of the tomographic image Gi so as to set off the displacement. Then, the image processor 230 executes the process from Step 3 and after shown in FIG. 8.

According to the modification, after positional offsetting of the tomographic image Gi attributed to movements of the eye E during scanning with a signal light LS is corrected, the accuracy in positional relation in the x-y direction between one tomographic image Gi to become a correction subject and other tomographic images G(i+1) and G(i−1) referred in the correction process can be enhanced. Therefore, it becomes possible to execute the process related to the present invention with high accuracy. Moreover, it is also possible to execute a positional correction in the depth-wise direction like the one that has been described in the above first example, along with the process of the second example.

[Image Processing Device]

The image processing device related to the present invention is now described. In the above embodiment, the arithmetic and control device 200 is used as the image processing device.

The image processing device according to the present invention comprises: a storage configured to store a tomographic image at each of a plurality of cross sections of a measurement object; and an image processor configured to execute an arithmetic operation based on a tomographic image at one cross section and other tomographic images at each of one or more cross sections other than the one cross section, thereby forming a new tomographic image at the one cross section. In the arithmetic and control device 200 of the above embodiment, the image storage 250 functions as a storage, and the image processor 230 functions as an image processor.

According to the image processing device, it is possible to increase the image quality of a tomographic image to be formed, compared with the conventional configuration of forming a tomographic image based on only the result of measurement at a single cross section. Further, by forming a 3-dimensional image based on these new tomographic images, it is possible to acquire a 3-dimensional image with higher image quality than conventional. Moreover, by forming a tomographic image at an arbitrary cross section based on this 3-dimensional image, it is possible to acquire a tomographic image with higher image quality than conventional.

[Program]

A program for controlling the device related to the present invention is now described. In the above embodiment, the control program 204a corresponds to the program.

The program causes a computer such as the arithmetic and control unit 200 that comprises a storage storing a tomographic image at each of a plurality of cross sections of a measurement object, to execute an arithmetic operation based on a tomographic image at one cross section and other tomographic images at each of one or more cross sections other than the one cross section and thereby form a new tomographic image at the one cross section.

According to the program, it is possible to increase the image quality of a tomographic image to be formed, compared with the conventional configuration of forming a tomographic image based on only the result of measurement at a single cross section. Further, by forming a 3-dimensional image based on these new tomographic images, it is possible to acquire a 3-dimensional image with higher image quality than conventional. Moreover, by forming a tomographic image at an optional cross section based on this 3-dimensional image, it is possible to acquire a tomographic image with higher image quality than conventional.

It is possible to properly apply modification for implementing various kinds of processes described in the above embodiment to the image processing device and program described above.

What is claimed is:

1. An optical image measurement device comprising:
an imaging forming part configured to form tomographic images $G(1)$-$G(m)$ at a plurality of cross sections of a measurement object,
an image processor configured to execute an arithmetic operation based on a tomographic image at one cross section of the plurality of cross sections and another tomographic image at each of one or more cross sections other than the one cross section, thereby forming a new tomographic image at the one cross section, wherein
the image processor is configured to, for a cross section corresponding to each scanning line Ri ($1<i<m$), execute an arithmetic operation based on a tomographic image Gi at the cross section, a tomographic image $G(i+1)$ at a cross section corresponding to a scanning line $R(i+1)$, and a tomographic image $G(i-1)$ at a cross section corresponding to a scanning line $R(i-1)$, so as to form a new tomographic image $G(i)$ at the cross section corresponding to the scanning line Ri to recreate new tomographic images $G(2)$-$G(m-1)$.

2. The optical image measurement device according to claim 1, wherein:
the image processor executes the arithmetic operation based on the tomographic image at the one cross section and the other tomographic image at a cross section adjacent to the one cross section, thereby forming the new tomographic image.

3. The optical image measurement device according to claim 1, wherein:
the image processor executes the arithmetic operation based on a pixel value of a pixel of the tomographic image at a specific position in the one cross section and a pixel value of a pixel of the other tomographic image at a position corresponding to the specific position, thereby obtaining a pixel value of a pixel of the new tomographic image at the specific position.

4. The optical image measurement device according to claim 2, wherein:
the image processor executes the arithmetic operation based on a pixel value of a pixel of the tomographic image at a specific position in the one cross section and a pixel value of a pixel of the other tomographic image at a position corresponding to the specific position, thereby obtaining a pixel value of a pixel of the new tomographic image at the specific position.

5. The optical image measurement device according to claim 3, wherein:
the image processor calculates an average value of the pixel value of the pixel of the tomographic image at the specific position and the pixel value of the pixel of the other tomographic image at the position corresponding to the specific position, as the pixel value of the pixel of the new tomographic image at the specific position.

6. The optical image measurement device according to claim 4, wherein:
the image processor calculates an average value of the pixel value of the pixel of the tomographic image at the specific position and the pixel value of the pixel of the other tomographic image at the position corresponding to the specific position, as the pixel value of the pixel of the new tomographic image at the specific position.

7. The optical image measurement device according to claim 3, wherein:
the image processor calculates a median of the pixel value of the pixel of the tomographic image at the specific position and the pixel value of the pixel of the other tomographic image at the position corresponding to the specific position, as the pixel value of the pixel of the new tomographic image at the specific position.

8. The optical image measurement device according to claim 4, wherein:
the image processor calculates a median of the pixel value of the pixel of the tomographic image at the specific position and the pixel value of the pixel of the other tomographic image at the position corresponding to the specific position, as the pixel value of the pixel of the new tomographic image at the specific position.

9. An image processing device comprising:
a storage configured to store tomographic images $G(1)$-$G(m)$ at a plurality of cross sections of a measurement object; and
an image processor configured to execute an arithmetic operation based on a tomographic image at one cross section of the plurality of cross sections and another tomographic image at each of one or more cross sections other than the one cross section, thereby forming a new tomographic image at the one cross section, wherein
the image processor is configured to, for a cross section corresponding to each scanning line $Ri$ ($1<i<m$), execute an arithmetic operation based on a tomographic image $Gi$ at the cross section, a tomographic image $G(i+1)$ at a cross section corresponding to a scanning line $R(i+1)$, and a tomographic image $G(i-1)$ at a cross section corresponding to a scanning line $R(i-1)$, so as to form a new tomographic image $G(i)$ at the cross section corresponding to the scanning line $Ri$ to recreate new tomographic images $G(2)$-$G(m-1)$.

* * * * *